United States Patent [19]
Suzawa et al.

[11] Patent Number: 6,103,236
[45] Date of Patent: Aug. 15, 2000

[54] TOXIN CONJUGATES

[75] Inventors: Toshiyuki Suzawa, Yamato; Motoo Yamasaki, Machida; Satoru Nagamura, Hofu; Hiromitsu Saito, Kawasaki; So Ohta, Sunto-gun; Nobuo Hanai, Sagamihara, all of Japan

[73] Assignee: Kyowa Hakko Kogyo Co., Ltd., Tokyo, Japan

[21] Appl. No.: 08/981,416

[22] PCT Filed: May 10, 1996

[86] PCT No.: PCT/JP96/01241

§ 371 Date: Nov. 10, 1997

§ 102(e) Date: Nov. 10, 1997

[87] PCT Pub. No.: WO96/35451

PCT Pub. Date: Nov. 14, 1996

[30] Foreign Application Priority Data

May 10, 1995 [JP] Japan .................................. 7-111933

[51] Int. Cl.⁷ .......................... A61K 39/395; C07K 16/00
[52] U.S. Cl. ..................... 424/183.1; 424/178.1; 424/193.1; 424/236.1; 530/391.1; 530/391.7; 530/391.9
[58] Field of Search ........................ 435/331; 530/391.7, 530/391.9, 391.1, 866, 867; 424/179.1, 193.1, 183.1, 236.1, 178.1, 237.1

[56] References Cited

U.S. PATENT DOCUMENTS

| 3,590,028 | 6/1971 | Arcamone et al. . |
| 4,671,958 | 6/1987 | Rodwell . |
| 4,863,935 | 9/1989 | Shida et al. . |

FOREIGN PATENT DOCUMENTS

| 60-67433 | of 0000 | Japan . |
| 63-150282 | of 0000 | Japan . |
| 63-256336 | of 0000 | Japan . |
| 63-35575 | of 0000 | Japan . |
| WO86/04145 | 7/1986 | WIPO . |
| WO91/18012 | 11/1991 | WIPO . |
| WO92/01470 | 6/1992 | WIPO . |
| WO93/08838 | 5/1993 | WIPO . |

*Primary Examiner*—Keith D. MacMillan
*Assistant Examiner*—P. Ponnahuri
*Attorney, Agent, or Firm*—Antonelli, Terry, Stout & Kraus, LLP

[57] ABSTRACT

The present invention relates to a toxin conjugate in which a residue derived from a compound having an affinity for a target cell is bound to a toxin through a spacer comprising polyalkylene glycol and dipeptide.

11 Claims, 2 Drawing Sheets

TOXIN CONJUGATES

This application is a 371 of PCT/JP96/01241, filed on May 10, 1996.

TECHNICAL FIELD

The present invention relates to toxin conjugates in which a toxin is bound through a spacer to a residue derived from a compound which has an affinity for a target cell, for example, a residue derived from an antibody or antibody fragment which is specific to a cancer. The toxin conjugate obtained by the present invention inhibits the growth of a target cell selectively and efficiently, and is useful as an active ingredient of an antitumor agent.

effects is a big problem to be solved, and comprehensive research has so far been made to this end. Specifically, in recent years, research on drug delivery systems has been pursued aiming at alleviation of toxicity, maintenance of concentration in blood and improvement of affinity for a cancer cell. For example, the modification with a copolymer of divinyl ether-maleic anhydride (Japanese Published Unexamined Patent Application No. 67490/85), and the modification with dextran [Cancer Treatment Reports, 66, 107 (1982)] have been reported.

Further, antibody conjugates (toxin conjugates) having a specificity to a cancer cell have been studied. Some examples of such conjugates are shown below [Bioconjugate Chem., 1, 13 (1990)].

| stracture | toxin |
|---|---|
| Ab-Lys-NH—C(=O)—CH$_2$—CH$_2$—C(=O)—O-toxin | vinblastine |
| Ab-Lys-NH—C(=O)—...—S—S-toxin (with R, H) | risin A<br>diphtheria toxin A<br>abrin A |
| Ab-carbohydrate—C(H)=N—NH—C(=O)—toxin | vinblastine hydrazide<br>methotrexate hydrazide |
| Ab-Lys-NH—C(=O)—aconitic acid—C(=O)—NH-toxin | anthracycline |
| Ab-Lys-NH—C(=S)—NH-toxin | chelates of indium and yttrium |
| Ab-Lys-NH—C(=O)—C$_6$H$_4$—C(H)=N—NH—C(=O)-toxin | metal chelates |
| Ab-carbohydrate—C(=O)—NH—N=C(R)-toxin | anthracycline |

BACKGROUND ART

Anthracycline anticancer compounds so far known include daunomycin (U.S. Pat. No. 3,590,028) and adriamycin (U.S. Pat. No. 3,590,028), which are in wide clinical use as anticancer agents. However, side effects of these compounds have been reported; for example, adriamycin is known to have side effects such as cardial toxicity and marrow depression [Cancer Chemotherapy and Pharmacology, 4, 5–10 (1980)]. Alleviation of such side There are some other reports relating to antibody conjugates [Japanese Published Unexamined Patent Application No. 67433/85; Japanese Published Unexamined Patent Application No. 35575/88; Japanese Published Unexamined Patent Application No. 150282/88; Japanese Published Unexamined Patent Application No. 246336/88; Biochem. J., 173, 723 (1978); Cancer Res., 50, 6600 (1990); Science, 261, 212 (1993); Bioconjugate Chem., 4, 275 (1993); Bioconjugate Chem., 4, 251 (1993); Bioconjugate Chem., 5, 88

(1994); Bioconjugate Chem., 5, 31 (1994); and Bioconjugate Chem., 5, 246 (1994)].

There are also known examples in which low molecular weight polyethylene glycol is used as a spacer [Proc. Natl. Acad. Sci. USA, 88, 9287 (1991); PCT National Publication No. 508856/93; and Bioconjugate Chem., 4, 455 (1993)], and examples of the modification of an antibody with polyethylene glycol (WO 93/08838 and WO 86/04145). Further, the use of a spacer containing a peptide has been reported [U.S. Pat. No. 4,671,958; PCT National Publication No. 502886/93; and Bioconjugate Chem., 4, 10 (1993)].

DISCLOSURE OF THE INVENTION

The present inventors made intensive studies in search of an excellent toxin conjugate which kills tumor cells selectively. As a result, the inventors have found that a conjugate having a spacer which is specifically cleaved when introduced into a specific cell can be obtained by chemically binding a toxin to a compound which has a specific affinity for a cancer cell through a novel spacer comprising polyethylene glycol and dipeptide. Thus the present invention has been completed.

The present invention relates to a toxin conjugate in which a residue derived from a compound having an affinity for a target cell is bound to a toxin through a spacer comprising polyalkylene glycol and dipeptide.

Typical examples of the conjugates of the present invention are toxin conjugates represented by general formula (A):

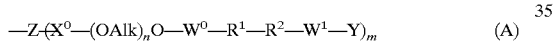

wherein Z represents a residue derived from a compound having an affinity for a target cell; $Y^1$ represents a toxin; $R^1$ and $R^2$, which may be the same or different, each represents an amino acid residue; Alk represents alkylene; n represents an integer of 1–1000; and m represents an integer of 1–100. Although $X^0$, $W^0$ and $W^1$ are not specifically defined, examples of their representations are as follows: $X^0$ represents —COAlk$^1$—, —SAlk$^1$—, —COOAlk$^1$—, —CONHAlk$^1$—, —COAlk$^1$CO—,

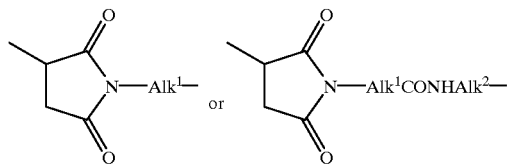

$W^0$ represents CO, —Alk$^1$CO—, or —Alk$^1$S—; and $W^1$ represents a single bond, S, —OAlk$^1$CO—, —NHAlk$^1$CO—, —NHAlk$^1$NH—,

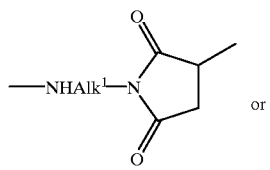

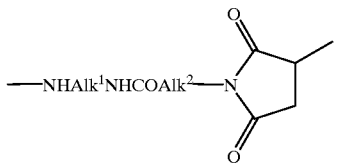

In the above formulae, Alk$^1$ and Alk$^2$, which may be the same or different, each represents a straight-chain or branched alkylene having 1–8 carbon atoms, such as methylene, ethylene, propylene, isopropylene, butylene, isobutylene, pentylene, hexylene, heptylene, and octylene.

Particularly, preferred toxin conjugates are compounds represented by general formula (I):

wherein $X^1$ represents CO, S or

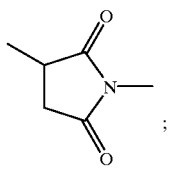

w represents a single bond or

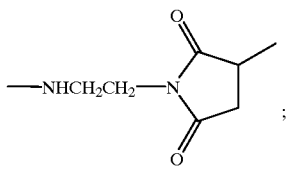

and Z, $Y^1$, $R^1$, $R^2$, n and m have the same meanings as defined above. The compounds represented by general formula (I) are hereinafter referred to as Compounds (I), and the same applies to the compounds of other formula numbers.

In the definitions of the above-described groups, the alkylene moiety of the alkylene and the polyalkylene glycol means a straight-chain or branched alkylene having 1–8 carbon atoms such as methylene, ethylene, propylene, isopropylene, butylene, isobutylene, pentylene, hexylene, heptylene, and octylene. Examples of the compounds which have an affinity for a target cell are compounds having a structure capable of binding to $X^1$ such as COOH, NH, SH, and OH, e.g., receptor ligands such as epidermal growth factors (EGF) and transferrin having an affinity for a target cell, adhesion molecules represented by the arginine-glycine-aspartic acid sequence, and proteins and peptides such as antibodies and antibody fragments. Preferred examples are antibodies and antibody fragments. The antibodies include polyclonal antibodies and monoclonal antibodies produced according to known methods which belong to immunoglobulin (Ig) classes such as IgG, IgA, IgM, and IgE, and immunoglobulin subclasses, for example, IgG$_1$, IgG$_2$, IgG$_3$, and IgG$_4$ in the case of IgG. Preferred examples are KM-641 antibody which is an antibody against ganglioside GD$_3$ which is highly expressed in a cancer cell (Japanese Published Unexamined Patent Application No. 176791/93), KM-231 (AMC-462) antibody which is an antibody against sialyl Lewis a (Japanese Published Unexamined Patent Application No. 021562/88), and NL-1 antibody which is an antibody against common human acute lymphatic leukemia cell antigen (CALLA) [Proc. Natl. Acad. Sci. USA 79, 4386–4390 (1982)]. Examples of the antibody fragments are F(ab')$_2$ obtained by treating the above-mentioned antibodies with a proteolytic enzyme such as pepsin, Fab' obtained by reducing F(ab')$_2$ with mercaptan, and Fab obtained by degrading the antibodies with a proteolytic enzyme such as papain, trypsin, chymotrypsin, and plasmin. F(ab')$_2$, Fab', and Fab are known as well as methods for producing them [Immunochemistry, Yuichi Yamamura et al., p. 461, Asakura Shoten (1973)]. Examples of the toxins are toxins having a structure capable of condensing with a carboxyl group of the terminal amino acid $R^2$ or capable of attaching to a double bond of maleinimide, such as NH, SH and OH, e.g., anthracycline compounds such as adriamycin (U.S. Pat. No. 3,590,028) and daunorubicin (U.S. Pat. No. 3,616,242), duocarmycin derivatives such as DC-88A derivatives (Japanese Published Unexamined Patent Application No. 288879/90) and the compounds described in Reference Examples, mitomycin A, mitomycin C, and protein toxins such as ricin A, diphtheria toxin, and Pseudomonas exotoxin. Examples of the amino acid residues are an alanine residue, a leucine residue, a glycine residue, a proline residue and a valine residue.

The abbreviations used herein have the following meanings, unless otherwise specified.

The abbreviations for amino acids and their protecting groups follow the recommendations by IUPAC-IUB Joint Commission on Biochemical Nomenclature [Biochemistry, 11, 1726 (1972)].

Ala: L-Alanine
Val: L-Valine
Pro: L-Proline
Gly: Glycine
DMF: N,N-Dimethylformamide
DMSO: Dimethylsulfoxide
THF: Tetrahydrofuran
TFA: Trifluoroacetic acid
NMM: N-Methylmorpholine
Bzl: Benzyl
tBu: tert-Butyl
Z: Benzyloxycarbonyl
Pic: Picolyl
HONSu: N-Hydroxysuccinimide
ONSu: Succinimidoxy
DCC: N,N'-Dicyclohexylcarbodiimide
DCU: N,N'-Dicyclohexylurea
ADM: Adriamycin
DNR: Daunorubicin
HOBt: N-Hydroxybenzotriazole
PyBOP: Benzotriazol-1-yloxytripyrrolidinophosphonium hexafluorophosphate
EDC: 1-(3-Dimethylaminopropyl)-3-ethylcarbodiimide
DMAP: 4-(N,N-Dimethylamino) pyridine
PEG: COCH$_2$ (OCH$_2$CH$_2$)$_n$OCH$_2$CO
HPLC: High performance liquid chromatography
NMR: Nuclear magnetic resonance The processes for preparing Compounds (I) and polyethylene glycol derivatives represented by general formula (II):

$$X^2\text{—}CH_2(OCH_2CH_2)_n OCH_2CO\text{—}R^1\text{—}R^2\text{—}Y^2 \quad (II)$$

(wherein $X^2$ represents carboxyl, mercapto or

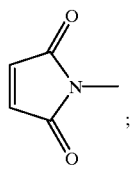

;

$Y^2$ represents hydroxyl or

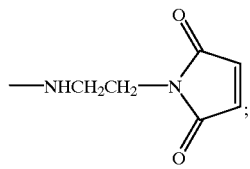

;

and $R^1$, $R^2$ and n have the same meanings as defined above) are described below.

Process 1: Process for preparing Compound (Ia), i.e., Compound (I) wherein Z is a group having N, S or O, $X^1$ is CO, and W is a single bond Compound (Ia) can be prepared according to the following reaction steps.

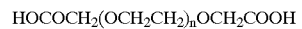
(III)

HOCOCH$_2$(OCH$_2$CH$_2$)$_n$OCH$_2$COOH $A^1$-Hal (IV) | step 1

(V)

$A^1$OCOCH$_2$(OCH$_2$CH$_2$)$_n$OCH$_2$COOH

H—$R^1$—$R^2$—OA$^2$ (VI) | step 2

(VII)

$A^1$OCOCH$_2$(OCH$_2$CH$_2$)$_n$OCH$_2$CO—$R^1$—$R^2$—OA$^2$

| step 3

(VIII)

$A^1$OCOCH$_2$(OCH$_2$CH$_2$)$_n$OCH$_2$CO—$R^1$—$R^2$—OH

| step 4

(IX)

($A^1$OCOCH$_2$(OCH$_2$CH$_2$)$_n$OCH$_2$CO—$R^1$—$R^2$—OA$^3$)

|

(X)

$A^1$OCOCH$_2$(OCH$_2$CH$_2$)$_n$OCH$_2$CO—$R^1$—$R^2$—Y$^1$

| step 5

(XI)

HOCOCH$_2$(OCH$_2$CH$_2$)$_n$OCH$_2$CO—$R^1$—$R^2$—Y$^1$

| step 6

-continued

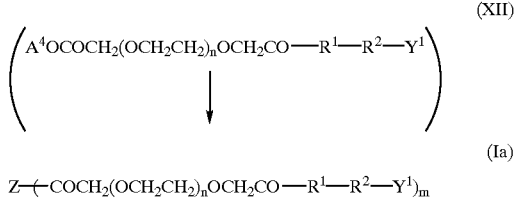

$$Z \leftarrow COCH_2(OCH_2CH_2)_nOCH_2CO-R^1-R^2-Y^1)_m \quad \text{(Ia)}$$

(In the formulae, $A^1$ and $A^2$, which may be the same or different, each represents a carboxylic acid protecting group; $A^3$ and $A^4$, which may be the same or different, each represents a carbxylic acid activating group; Hal represents halogen; $Z^1$ represents a group having N, S or O in the definition of Z; and $Y^1$, $R^1$, $R^2$ and n have the same meanings as defined above.)

Examples of the carboxylic acid protecting group are carboxylic acid protecting groups used in ordinary peptide synthesis (Fundamentals and Experiments of Peptide Synthesis, Nobuo Izumiya et al., Maruzen) such as tBu, Bzl, and Pic. An example of the carboxylic acid activating group is ONSu. The halogen means a chlorine atom, a bromine atom or an iodine atom.

(Step 1)

Compound (V) can be obtained by reaction of polyethylene glycol dicarboxylic acid (III) with Compound (IV) in an amount of 0.1 to 1 equivalent, preferably, 0.5 equivalent in a solvent such as DMF in the presence of a base such as potassium carbonate at −50 to 30° C. for 1 to 24 hours. Diester and unreactive dicarboxylic acid contained in the obtained product can be removed by partition column chromatography, column chromatography using adsorption resins, reversed-phase silica gel, alumina, diatomaceous earth, or ion-exchange resins, preferably, silica gel column chromatography or thin layer chromatography.

(Step 2)

Compound (VII) can be obtained by condensing Compound (V) with Compound (VI) obtained according to an ordinary liquid-phase peptide synthesis method (Fundamentals and Experiments of Peptide Synthesis, Nobuo Izumiya et al., Maruzen) in a solvent in the presence of a base in an amount of 1 to 2 equivalents, using a condensing agent in an amount of 1 to 10 equivalents, preferably 1 to 2 equivalents. Examples of the base are triethylamine and NMM, examples of the condensing agent are ordinary amino acid condensing reagents such as DCC and EDC, and examples of the solvent are methylene chloride, chloroform and DMF. The reaction is carried out by stirring at 0 to 30° C. for 1 to 24 hours.

It is preferred that $A^2$ used as the carboxylic acid protecting group of Compound (VI) is a group which can be selectively removed separately from $A^1$ of Compound (V).

Compound (VII) can also be obtained by condensing Compound (V) with HONSu, HOBt, or the like in an amount of 1 to 10 equivalents, preferably 1 to 2 equivalents in a solvent in the presence of an equivalent amount of a base, using a condensing agent in an amount of 1 to 5 equivalents, preferably 1 to 2 equivalents to obtain an active ester, and then by subjecting the obtained ester to reaction with Compound (VI) at 0 to 30° C. for 1 to 24 hours. As the base, condensing agent and solvent, those which are described above can be used.

(Step 3)

Compound (VIII) can be obtained by selectively removing the protecting group $A^2$ from Compound (VII) according to a method for the removal of a protecting group used in ordinary peptide synthesis (Fundamentals and Experiments of Peptide Synthesis, Nobuo Izumiya et al., Maruzen).

(Step 4)

Compound (X) can be obtained by condensing Compound (VIII) with an equivalent amount of a toxin in a solvent in the presence of a base in an amount of 1 to 2 equivalents, using a condensing agent in an amount of 1 to 10 equivalents, preferably 1 to 2 equivalents. Examples of the base are triethylamine and NMM, examples of the condensing agent are ordinary amino acid condensing reagents such as DCC and EDC, and examples of the solvent are methylene chloride, chloroform and DMF. The reaction is carried out by stirring at −30 to 30° C. for 1 to 24 hours.

Compound (X) can also be obtained by condensing Compound (VIII) with HONSu, HOBt, or the like in an amount of 1 to 10 equivalents, preferably 1 to 2 equivalents in a solvent in the presence of an equivalent amount of a base, using a condensing agent in an amount of 1 to 5 equivalents, preferably 1 to 2 equivalents to obtain an active ester (IX), and then by subjecting the obtained ester to reaction with a toxin at −30 to 30° C. for 1 to 24 hours. As the base, condensing agent and solvent, those which are described above can be used.

(Step 5)

Compound (XI) can be obtained by removing the protecting group $A^1$ from Compound (X) according to a method for the removal of a protecting group used in ordinary peptide synthesis (Fundamentals and Experiments of Peptide Synthesis, Nobuo Izumiya et al., Maruzen). In the case, for example, where Bzl is used as $A^1$ and tBu as $A^2$, which are to be removed in Steps 3 and 5, respectively, deprotection is carried out according to ordinary methods for selectively removing amino acid protecting groups such as hydration in the presence of a palladium carbon catalyst for $A^1$, and trifluoroacetic acid treatment for $A^2$, whereby $A^1$ and $A^2$ can be selectively removed in each step. It is possible to use the above combination of $A^1$ and $A^2$ in reverse and to reverse the order of deprotection steps.

Compound (XI) can also be obtained by removing the protecting group $A^1$ from Compound (IX) obtained in Step 4 according to the method of Step 5, and then subjecting the obtained compound to reaction with a toxin according to the method of Step 2.

(Step 6)

Compound (Ia) can be obtained from Compound (XI) and a compound which has an affinity for a target cell and has NH, SH, or OH in the molecule according to the method of Step 2. The compounds having an affinity for a target cell, such as proteins and peptides, are liable to be denatured and inactivated in an organic solvent, and it is preferred to carry out the above reaction under mild conditions, e.g. in an aqueous solution. In this case, the reaction is carried out by dissolving a compound having an affinity for a target cell in a buffer such as a phosphate buffer or a borate buffer (pH 6–8), and adding to the solution Compound (XI) in an amount of 1 to 500 equivalents, preferably, 1 to 50 equivalents, and a condensing agent such as EDC, followed by stirring at 0 to 30° C. for 1 to 48 hours. Alternatively, the reaction may be carried out by obtaining an active ester (XII) according to the method of Step 2, and adding to a solution of a compound having an affinity for a target cell in a buffer (pH 6–8) the obtained active ester in an amount of 1 to 500 equivalents, preferably 1 to 50 equivalents in the presence of 0 to 10%, preferably 0 to 5% DMSO or DMF, followed by stirring at 0 to 30° C. for 1 to 48 hours.

Process 2: Process for preparing Compound (Ib), i.e., Compound (I) wherein Z is a group having N, S or O, $X^1$ is CO, and W is

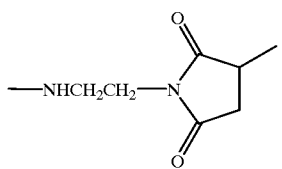

Compound (Ib) can be prepared according to the following reaction steps.

 (VIII)

↓ step 7

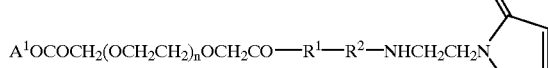 (XIII)

↓ step 8

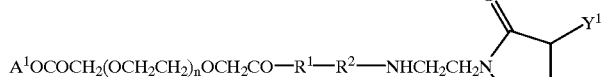 (XIV)

↓ step 9

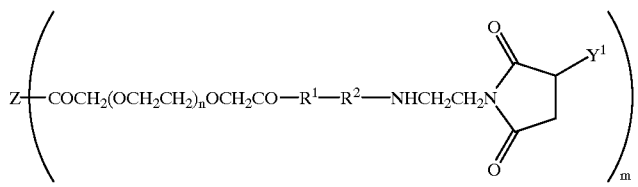 (Ib)

(In the formulae, $A^1$, $Y^1$, $Z^1$, $R^1$, $R^2$ and n have the same meanings as defined above).

(Step 7)

Compound (XIII) can be obtained from Compound (VIII) and aminoethyl maleimide according to the method of Step 2.

(Step 8)

Compound (XIV) can be obtained by subjecting Compound (XIII) to reaction with a toxin. The reaction is carried out by dissolving a toxin in a buffer such as a phosphate buffer and a borate buffer (pH 6–8), and adding Compound (XIII) in an amount of 1 to 50 equivalents to the solution, followed by stirring at 0 to 30° C. for 1 to 48 hours.

(Step 9)

Compound (Ib) can be obtained from Compound (XIV) according to the methods of Steps 5 and 6.

Process 3: Process for preparing Compound (Ic), i.e., Compound (I) wherein Z is a group having CO, $X^1$ is S, and W is a single bond Compound (Ic) can be prepared according to the following reaction steps.

$HSCH_2(OCH_2CH_2)_nOCH_2COOA^1$ (XV)

↓ step 10

-continued $A^4SCH_2(OCH_2CH_2)_nOCH_2COOA^1$ (XVI)

↓ step 11

$A^4SCH_2(OCH_2CH_2)_nOCH_2COOH$ (XVII)

↓ step 12

$A^4SCH_2(OCH_2CH_2)_nOCH_2CO—R^1—R^2—OH$ (XVIII)

↓ step 13

(XIX)

A⁴SCH₂(OCH₂CH₂)ₙOCH₂CO—R¹—R²—Y¹

| step 14

(XX)

HSCH₂(OCH₂CH₂)ₙOCH₂CO—R¹—R²—Y¹

| step 15

(Ic)

Z—(—SCH₂(OCH₂CH₂)ₙOCH₂CO—R¹—R²—Y¹)ₘ

(In the formulae, $A^4$ represents a thiol protecting group; $Z^2$ represents a group having CO in the definition of Z; and $A^1$, $Y^1$, $R^1$, $R^2$ and n have the same meanings as defined above.)

Examples of the thiol protecting group are benzyl, picolyl, and nitrobenzyl.

The starting compound (XV) can be obtained according to the method for the synthesis of polyethylene glycol derivatives described in Poly (Ethylene Glycol) Chemistry: Biotechnical and Biomedical Applications (J. M. Harris, Ed., Plenum, N.Y. 1992).

(Step 10)

Compound (XVI) can be obtained by protecting the thiol group of Compound (XV) according to a method for introducing a protecting group used in ordinary peptide synthesis (Fundamentals and Experiments of Peptide Synthesis, Nobuo Izumiya et al., Maruzen).

(Step 11)

Compound (XVII) can be obtained from Compound (XVI) according to the method of Step 3.

(Step 12)

Compound (XVIII) can be obtained from Compound (XVII) according to the methods of Steps 2 and 3.

(Step 13)

Compound (XIX) can be obtained from Compound (XVIII) according to the method of Step 4.

(Step 14)

Compound (XX) can be obtained by deprotecting Compound (XIX) according to a method for removing a protecting group used in ordinary peptide synthesis (Fundamentals and Experiments of Peptide Synthesis, Nobuo Izumiya et al., Maruzen).

(Step 15)

Compound (Ic) can be obtained by binding Compound (XX) to a compound having an affinity for a target cell and having COOH in the molecule by a method such as the activation of a thiol group described in J. Applied Biochem., 6, 56–63 (1984).

Process 4: Process for preparing Compound (Id), i.e., Compound (I) wherein Z is a group having N, S or O, $X^1$ is

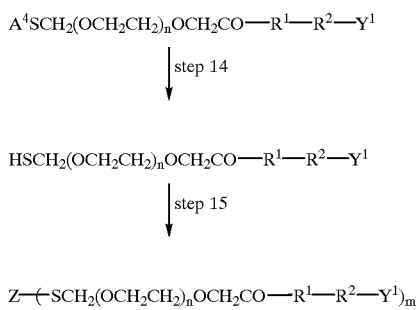

and W is a single bond, and Compound (IId), i.e., Compound (II) wherein $X^2$ is (maleimide structure)

and $Y^2$ is hydroxyl.

Compound (Id) and Compound (IId) can be prepared according to the following reaction steps.

(XXI)

(maleimide)-NCH₂(OCH₂CH₂)ₙOCH₂COOA¹

| step 16

(XXII)

(maleimide)-NCH₂(OCH₂CH₂)ₙOCH₂COOH

| step 17

(IId)

(maleimide)-NCH₂(OCH₂CH₂)ₙOCH₂CO—R¹—R²—OH

| step 18

(XXIII)

(maleimide)-NCH₂(OCH₂CH₂)ₙOCH₂CO—R¹—R²—Y¹

| step 19

(Id)

Z—(—(succinimide)-NCH₂(OCH₂CH₂)ₙOCH₂CO—R¹—R²—Y¹)ₘ

(In the formulae, $A^1$, $Y^1$, $Z^1$, $R^1$, $R^2$ and n have the same meanings as defined above.)

The starting compound (XXI) can be obtained according to the method for the synthesis of polyethylene glycol derivatives described in Poly (Ethylene Glycol) Chemistry: Biotechnical and Biomedical Applications (J. M. Harris, Ed., Plenum, N.Y. 1992).

(Step 16)

Compound (XXII) can be obtained from Compound (XXI) according to the method of Step 3.

(Step 17)

Compound (IId) can be obtained from Compound (XXII) according to the methods of Steps 2 and 3.

(Step 18)

Compound (XXIII) can be obtained from Compound (IId) according to the method of Step 4.

(Step 19)

Compound (Id) can be obtained from Compound (XXIII) and a compound having an affinity for a target cell and having NH, SH or OH in the molecule according to the method of Step 8.

Process 5: Process for preparing Compound (IIa), i.e., Compound (II) wherein $X^2$ is carboxyl and $Y^2$ is hydroxyl (Step 20)

Compound (IIa) can be obtained from Compound (VIII) according to the method of Step 3.

Process 6: Process for preparing Compound (IIb), i.e., Compound (II) wherein $X^2$ is carboxyl and $Y^2$ is

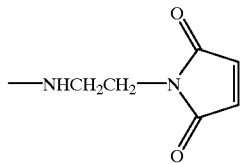

(Step 21)

Compound (IIb) can be obtained from Compound (XIII) according to the method of Step 3.

Process 7: Process for preparing Compound (IIc), i.e., Compound (II) wherein $X^2$ is mercapto and $Y^2$ is hydroxyl (Step 22)

Compound (IIc) can be obtained from Compound (XVIII) according to the method of Step 14.

Compounds (I) and (II) having the desired groups at the desired positions can be obtained by combining the above-described methods appropriately.

The intermediates and desired compounds in the above-described processes can be isolated and purified by purification methods such as filtration, extraction, washing, drying, concentration, recrystallization, various kinds of column chromatography, e.g. silica gel chromatography, ion-exchange chromatography, reversed-phase chromatography, and gel filtration chromatography, and dialysis using an ordinary semipermeable membrane. The intermediates can be subjected to the subsequent reaction without a specific purification treatment.

Examples of Toxin Conjugates (I) obtained by the above-described processes are shown in Table 1.

TABLE 1

| Compound No. | Structure |
|---|---|
| Ia-1 | NL-1-(PEG-Ala-Val-ADM)$_m$ |
| Ia-2 | NL-1-(PEG-Ala-Pro-ADM)$_m$ |
| Ia-3 | NL-1-(PEG-Gly-Pro-ADM)$_m$ |
| Ia-4 | KM-231-(PEG-Ala-Val-DNR)$_m$ |
| Ia-5 | KM-231-(PEG-Ala-Pro-DNR)$_m$ |
| Ia-6 | KM-231-(PEG-Gly-Pro-DNR)$_m$ |
| Ia-7 | NL-1-[PEG-Ala-Val-Compound (20) *]$_m$ |
| Ia-8 | NL-1-[PEG-Ala-Pro-Compound (20) *]$_m$ |
| Ia-9 | NL-1-[PEG-Gly-Pro-Compound (20) *]$_m$ |

TABLE 1-continued

| Compound No. | Structure |
|---|---|
| Ia-10 | KM-231-[PEG-Ala-Val-Compound (12) **]$_m$ |
| Ia-11 | KM-641-[PEG-Ala-Val-Compound (12) **]$_m$ |

*: Synthesized in Reference Example 17
**: Synthesized in Reference Example 15

The pharmacological activities of the toxin conjugates are shown below by Test Examples.

TEST EXAMPLE 1

The inhibitory effect of the toxin conjugates on cell growth was examined. Cervical cancer HeLaS3 cells (CALLA$^-$) having no expression of CALLA antigen and Burkitt lymphoma Daudi cells (CALLA$^+$) having an expression of CALLA antigen were used as target cell lines. Each of the target cell suspensions was put into wells of a 96-well flat plate in an amount of 50 μl ($1\times10^3$ cells/well), and cultured in a CO$_2$-incubator at 37° C. for 2 hours. After culturing, various dilutions of a toxin conjugate or a monoclonal antibody were respectively added in an amount of 50 μl, followed by further culturing in the CO$_2$-incubator at 37° C. for 68 hours. Then, 20 μl of $^3$H-thymidine (463 KBq/ml) was added to each well, and after 4 hours, the cells were harvested to determine the radioactivity of $^3$H-thymidine incorporated into the cells by using Matrix 96 (Packard Japan). The cell growth inhibiting activity was calculated according to the following equation.

$$\left(1 - \frac{\text{Radioactivity of treated cells}}{\text{Radioactivity of control cells}}\right) \times 100$$

As a result, Compound (Ia-3) and Compound (Ia-1) exhibited a little inhibitory effect on the growth of HeLaS3 cells at high concentrations, whereas they exhibited a remarkable inhibitory effect on the growth of Daudi cells even at very low concentrations. When Compound (Ia-9) or Compound (Ia-7) was added, an inhibitory effect was hardly observed on the growth of HeLaS3 cells, while a more specific inhibitory effect was observed on the growth of Daudi cells. Addition of the monoclonal antibody (NL-1) alone had little effect on the cell growth (refer to FIG. 1).

TEST EXAMPLE 2

The inhibitory effect of Compound (Ia-6) on cell growth was examined in the same manner as in Test Example 1. Cervical cancer HeLaS3 cells (sLe$^{a-}$) having no expression of sLe$^a$ antigen and large intestine cancer SW1116 cells (sLe$^{a+}$) having an expression of sLe$^a$ antigen were used as target cell lines. As a result, an inhibitory effect was observed on the growth of SW1116 cells, but not on the growth of HeLaS3 cells. When a monoclonal antibody (KM-231) alone was added, no cell growth inhibiting effect was observed on either of these strains. The antigen-specific cell growth inhibiting effect of the conjugate was thus confirmed (refer to Table 2).

TABLE 2

| Compound | Growth inhibiting effect (%) | |
|---|---|---|
| (12.5 μg/ml) | HeLaS3 | SW1116 |
| Compound (Ia-6) | 1.6 | 26.8 |
| KM-231 | 0.0 | 0.0 |

From the foregoing, the antigen-specific cell growth inhibiting effect of various kinds of conjugates and the utility of the spacers were confirmed.

TEST EXAMPLE 3

The inhibitory effect of Compound (Ia-10) on cell growth was examined. Cervical cancer HeLaS3 cells (sLe$^{a-}$) having no expression of sLe$^a$ antigen and large intestine cancer SWI116 cells (sLe$^{a+}$) having an expression of sLea antigen were used as target cell lines. Each of the target cell suspensions was put into wells of a 96-well flat plate in an amount of 50 μl (1×10$^3$ cells/well), and cultured in a CO$_2$-incubator at 37° C. for 2 hours. After culturing, various dilutions of the drug-monoclonal antibody conjugate or a monoclonal antibody were respectively added in an amount of 50 μl, followed by further culturing in the CO$_2$-incubator at 37° C. for 2 hours. Then, the cells in the plate were centrifuged, and immediately after removal of the supernatant, 100 μl of a medium was added, followed by further culturing for 64 hours. To each well was added 20 μl of $^3$H-thymidine (463 KBq/ml), and after 4 hours, the cells were harvested to determine the radioactivity of $^3$H-thymidine incorporated into the cells by using Matrix 96 (Packard Japan). The cell growth inhibiting activity was calculated according to the following equation.

$$\left(1 - \frac{\text{Radioactivity of treated cells}}{\text{Radioactivity of control cells}}\right) \times 100$$

As a result, Compound (Ia-10) exhibited an inhibitory effect on the growth of SW1116 cells, but no effect on the growth of HeLaS3 cells. When the monoclonal antibody (KM-231) alone was added, an inhibitory effect was slightly observed only on the growth of SA1116 cells. The antigen-specific cell growth inhibiting effect of the conjugate and the utility of the spacer were thus confirmed also in this assay system (refer to Table 3).

TABLE 3

| Compound | Growth Inhibiting effect (%) | |
|---|---|---|
| (75 μg/ml) | HeLaS3 | SW1116 |
| Compound (Ia-10) | 0.0 | 20.8 |
| KM-231 | 0.0 | 5.3 |

TEST EXAMPLE 4

Human myeloma SK-Ly-18 cells were suspended in RPMI-1640 medium containing 10 fetal calf serum at a concentration of 2×10$^8$ cells/ml, and the suspension was mixed with Matrigel (registered trademark; Becton Dickinson Labware, USA) in the ratio of 1:1 (v/v). The mixture (0.1 ml, 1×10$^7$ cells/mouse) was subcutaneously transplanted into BALB/C nu/nu mice (Clea Japan, Inc.). On the 7th day after the tumor transplantation, a drug-monoclonal antibody conjugate (amount corresponding to 7.5 mg/kg ADM) or ADM (7.5 mg/kg) was intravenously administered to the mice divided in groups each consisting of 5. A control group was given physiological saline in the same manner. The major axis and the minor axis of tumor were measured at intervals, and the tumor volume was calculated as an approximation value of an ellipsoid according to the following equation.

Tumor Volume (mm$^3$)=($a$×$b^2$)/2 a: major axis (mm) b: minor axis (mm)

The therapeutic effect on the transplanted tumor was evaluated in terms of V/V$_0$, the ratio of the tumor volume on the day of evaluation (V) to that on the day of drug administration (V$_0$).

As a result, a significant tumor growth was observed in the control group, and a remarkable tumor growth inhibiting effect was observed in Compound (Ia-1)- and Compound (Ia-3)-administered groups. On the other hand, a growth inhibiting effect was not observed in the test group to which the same quantity of ADM alone was given compared with the control group. The utility of the drug-monoclonal antibody conjugates was thus demonstrated (refer to FIG. 2).

BEST MODE FOR CARRYING OUT THE INVENTION

Figure 1:
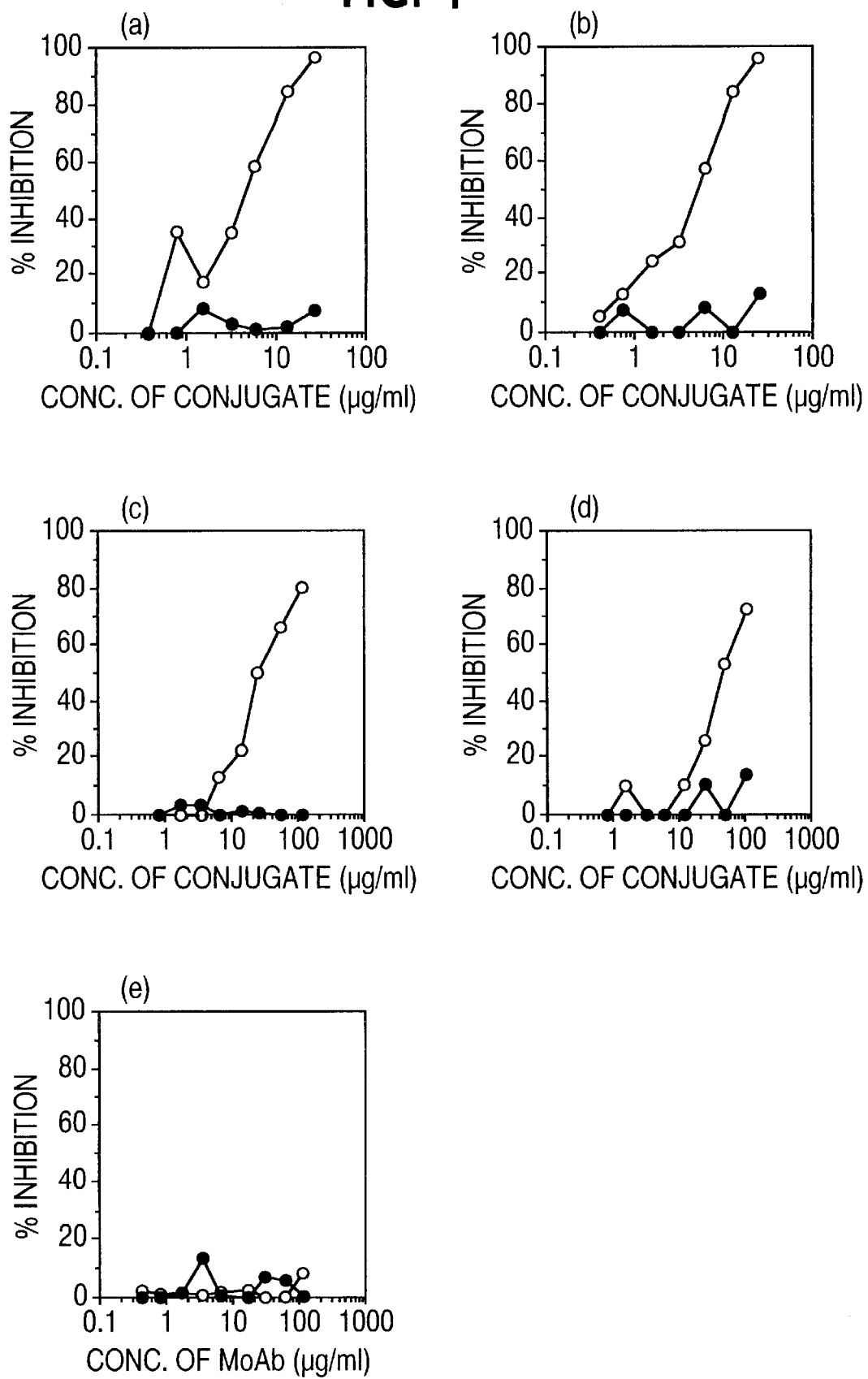
FIG. 1 shows the cell growth inhibiting effect of toxin conjugates and a monoclonal antibody.
  (a) The result obtained using Compound (Ia-3)
  (b) The result obtained using Compound (Ia-1)
  (c) The result obtained using Compound (Ia-9)
  (d) The result obtained using Compound (Ia-7)
  (e) The result obtained using NL-1
  ○ The result obtained using Daudi cells
  ● The result obtained using HeLaS3 cells
Figure 2:
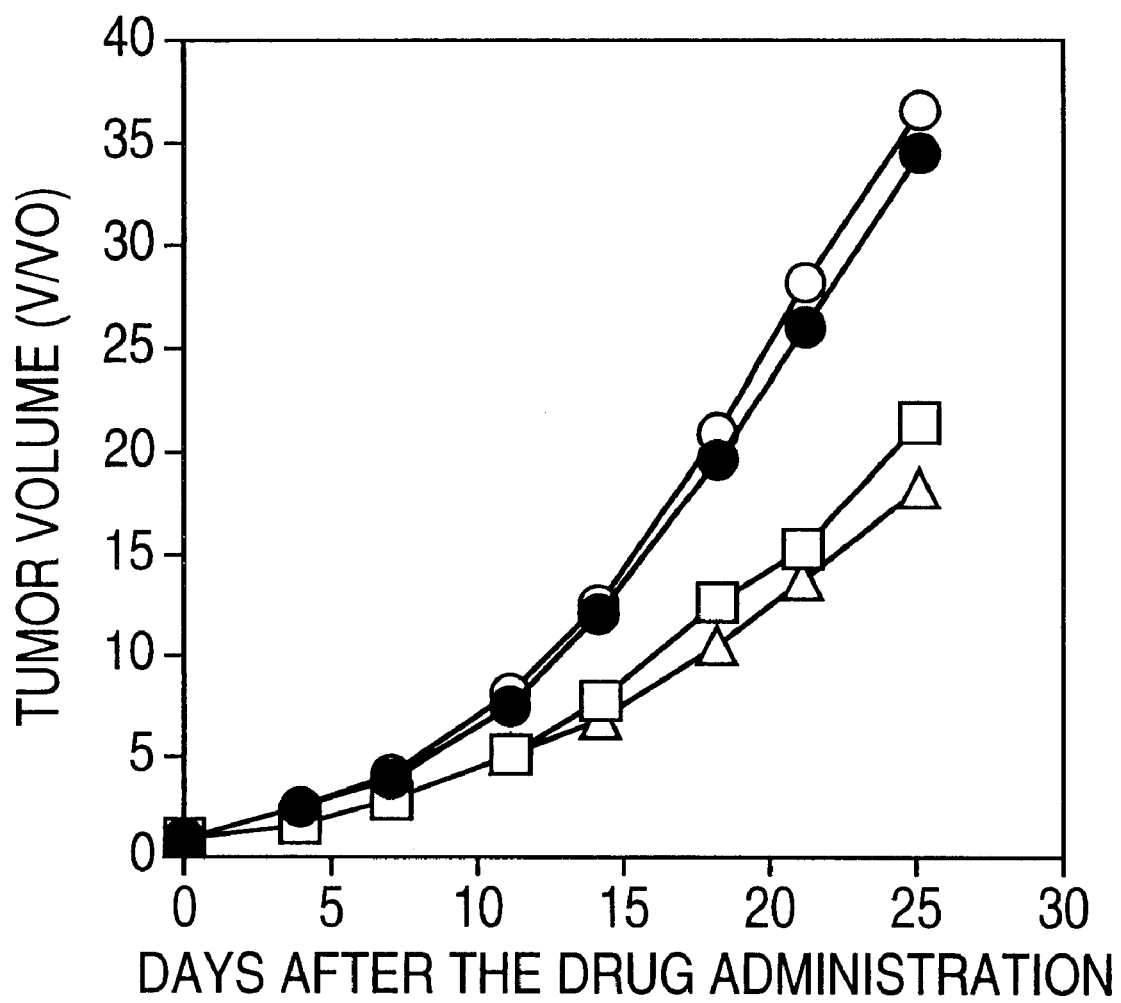
FIG. 2 shows the therapeutic effect of toxin conjugates and a drug on transplanted tumor.
  ● Control group
  □ The result obtained using Compound (Ia-1)
  Δ The result obtained using Compound (Ia-3)
  ○ The result obtained using ADM

Certain embodiments of the invention are illustrated in the following Examples and Reference Examples.

EXAMPLE 1

Toxin Conjugate (Ia-1): NL-1-(PEG-Ala-Val-ADM)$_m$

In 500 μl of methylene chloride was dissolved 275 μg (0.21 μmol) of Compound (XI-1) obtained in Reference Example 6, and 10 μl of a solution of HONSu (1.1 μmol) in methylene chloride (13.0 mg/ml) and 10 μl of a solution of DCC (1.1 μmol) in methylene chloride (22.0 mg/ml) were added successively thereto under ice cooling. After stirring under ice cooling for 1 hour and then at room temperature for 1.5 hours, the insoluble matter (DCU) was removed by filtration, and the solvent was removed from the filtrate under reduced pressure. The residue was dissolved in 70 μl of DMSO, and 1400 μl of a phosphate buffer was added thereto. To the resulting mixture was added 480 μl of an aqueous solution of NL-1 antibody (3.3 mg/ml), followed by gentle stirring at 4° C. for 24 hours. After the insoluble matter was removed with a filter (0.45 μm), the antibody fraction was purified by gel filtration HPLC [column: Superose 12 (Pharmacia Fine Chemicals, Inc.), developer: phosphate buffer, flow rate: 0.5 ml/min, detection: at the absorbance of 280 nm]. The desired fraction eluted was concentrated using a small-size ultrafiltration membrane (Millipore Corp., cut-off molecular weight: 5000) to give 771 μg of NL-1-(PEG-Ala-Val-ADM)$_m$ (protein content: 0.67 mg/ml) (yield: 49%).

In the obtained conjugate, the number of molecules of adriamycin bound was 2.2 per antibody molecule as calculated from the absorbance at 280 nm (absorption of protein= total absorption at 280 nm—absorption of adriamycin at 280 nm) and that at 495 nm (absorption of adriamycin, ε=1.21× 10$^4$ M$^{-1}$ cm$^{-1}$, ε280=ε495). It was confirmed that the affinity of the antibody is approximately equal to that of an unbound antibody according to the fluorescent antibody method described below.

<Measurement of an affinity of an antibody by the fluorescent antibody method>

To Daudi cells ($1\times10^6$) was added the above-described conjugate (10 μg/ml), and the mixture was subjected to reaction for 30 minutes under ice cooling. The cells were centrifuged and washed with a phosphate buffer three times, followed by removal of unreactive conjugate. To the resulting mixture was added 20 ml of FITC (fluorescein isothiocyanate)-labelled anti-mouse IgG antibody (Wako Pure Chemical Industries, Ltd., 30 times dilution) and the resulting mixture was subjected to reaction for 30 minutes under ice cooling. After centrifugation and washing with a phosphate buffer were repeated three times, measurement was carried out using a flow cytometer (EPICS Elite, Coulter). As a control, a reaction mixture of cells and the FITC-labelled anti-mouse IgG antibody was used.

EXAMPLE 2

Toxin Conjugate (Ia-2): NL-1-(PEG-Ala-Pro-ADM)$_m$

In 500 μl of methylene chloride was dissolved 289 μg (0.22 μmol) of Compound (XI-2) obtained in Reference Example 7, and 10 μl of a solution of HONSu (1.1 μmol) in methylene chloride (13.0 mg/ml) and 10 μl of a solution of DCC (1.1 μmol) in methylene chloride (23.1 mg/ml) were added successively thereto under ice cooling. After stirring under ice cooling for 1 hour and then at room temperature for 1.5 hours, the insoluble matter (DCU) was removed by filtration, and the solvent was removed from the filtrate under reduced pressure. The residue was dissolved in 95 μl of DMSO, and 1900 μl of a phosphate buffer was added thereto. To the resulting mixture was added 510 μl of an aqueous solution of NL-1 antibody (3.3 mg/ml), followed by gentle stirring at 4° C. for 24 hours. After the insoluble matter was removed with a filter (0.45 μm), the antibody fraction was purified by gel filtration HPLC and concentrated in the same manner as in Example 1 to give 1060 μg of NL-1-(PEG-Ala-Pro-ADM)$_m$ (protein content: 0.88 mg/ml) (yield: 63%).

In the obtained conjugate, the number of molecules of adriamycin bound was 1.8 per antibody molecule as calculated from the absorbances at 280 nm and 495 nm in the same manner as in Example 1. It was confirmed that the affinity of the conjugate was approximately equal to that of an unbound antibody according to the fluorescent antibody method described in Example 1.

EXAMPLE 3

Toxin Conjugate (Ia-3): NL-1-(PEG-Gly-Pro-ADM)$_m$

In 500 μl of methylene chloride was dissolved 259 μg (0.20 μmol) of Compound (XI-3) obtained in Reference Example 8, and 10 μl of a solution of HONSu (1.0 μmol) in methylene chloride (11.7 mg/ml) and 10 μl of a solution of DCC (1.0 μmol) in methylene chloride (21.0 mg/ml) were added successively thereto under ice cooling. After stirring under ice cooling for 1 hour and then at room temperature for 1.5 hours, the insoluble matter (DCU) was removed by filtration, and the solvent was removed from the filtrate under reduced pressure. The residue was dissolved in 76 μl of DMSO, and 1460 μl of a phosphate buffer was added thereto. To the resulting mixture was added 460 μl of an aqueous solution of NL-1 antibody (3.3 mg/ml), followed by gentle stirring at 4° C. for 24 hours. After the insoluble matter was removed with a filter (0.45 μm), the antibody fraction was purified by gel filtration HPLC and concentrated in the same manner as in Example 1 to give 912 μg of NL-1-(PEG-Gly-Pro-ADM)$_m$ (protein content: 0.76 mg/ml) (yield: 60%).

In the obtained conjugate, the number of molecules of adriamycin bound was 1.5 per antibody molecule as calculated from the absorbances at 280 nm and 495 nm in the same manner as in Example 1. It was confirmed that the affinity of the conjugate was approximately equal to that of an unbound antibody according to the fluorescent antibody method described in Example 1.

EXAMPLE 4

Toxin Conjugate (Ia-4): KM-231-(PEG-Ala-Val-DNR)$_m$

In 500 μl of methylene chloride was dissolved 96 μg (0.08 μmol) of Compound (XI-4) obtained in Reference Example 9, and 10 μl of a solution of HONSu (0.38 μmol) in methylene chloride (4.3 mg/ml) and 10 μl of a solution of DCC (0.37 μmol) in methylene chloride (7.7 mg/ml) were added successively thereto under ice cooling. After stirring under ice cooling for 1 hour and then at room temperature for 1 hour, the insoluble matter (DCU) was removed by filtration, and the solvent was removed from the filtrate under reduced pressure. The residue was dissolved in 27 μl of DMSO, and 114 μl of a phosphate buffer was added thereto. To the resulting mixture was added 563 μl of an aqueous solution of KM-231 antibody (1.0 mg/ml), followed by gentle stirring at 4° C. for 24 hours. After the insoluble matter was removed with a filter (0.45 μm), the antibody fraction was purified by gel filtration HPLC and concentrated in the same manner as in Example 1 to give 510 μg of KM-231-(PEG-Ala-Val-DNR)$_m$ (protein content: 0.85 mg/ml) (yield: 91%).

In the obtained conjugate, the number of molecules of daunorubicin bound was 3.1 per antibody molecule as calculated from the absorbance at 280 nm and that at 495 nm ($\epsilon=1.15\times10^4$ $M^{-1}$ $cm^{-1}$) in the same manner as in Example 1. It was confirmed that the affinity of the conjugate was approximately equal to that of an unbound antibody according to the fluorescent antibody method described in Example 1.

EXAMPLE 5

Toxin Conjugate (Ia-5): KM-231-(PEG-Ala-Pro-DNR)$_m$

In 500 μl of methylene chloride was dissolved 348 μg (0.27 μmol) of Compound (XI-5) obtained in Reference Example 10, and 10 μl of a solution of HONSu (1.4 μmol) in methylene chloride (15.7 mg/ml) and 10 μl of a solution of DCC (1.4 μmol) in methylene chloride (28.2 mg/ml) were added successively thereto under ice cooling. After stirring under ice cooling for 1 hour and then at room temperature for 1 hour, the insoluble matter (DCU) was removed by filtration, and the solvent was removed from the filtrate under reduced pressure. The residue was dissolved in 100 μl of DMSO, and 410 μl of a phosphate buffer was added thereto. To the resulting mixture was added 2.05 ml of an aqueous solution of KM-231 antibody (1.0 mg/ml), followed by gentle stirring at 4° C. for 24 hours. After the insoluble matter was removed with a filter (0.45 μm), the antibody fraction was purified by gel filtration HPLC and concentrated in the same manner as in Example 1 to give 2.0 mg of KM-231-(PEG-Ala-Pro-DNR)$_m$ (protein content: 1.36 mg/ml) (yield: 100%).

In the obtained conjugate, the number of molecules of daunorubicin bound was 1.9 per antibody molecule as calculated from the absorbances at 280 nm and 495 nm in the same manner as in Example 4. It was confirmed that the affinity of the conjugate was approximately equal to that of an unbound antibody according to the fluorescent antibody method described in Example 1, wherein SW1116 cells were used as the cells for evaluation.

EXAMPLE 6
Toxin Conjugate (Ia-6): KM-231-(PEG-Gly-Pro-DNR)$_m$

In 500 μl of methylene chloride was dissolved 154 μg (0.12 μmol) of Compound (XI-6) obtained in Reference Example 11, and 10 μl of a solution of HONSu (0.61 μmol) in methylene chloride (7.0 mg/ml) and 10 μl of a solution of DCC (0.61 μmol) in methylene chloride (12.6 mg/ml) were added successively thereto under ice cooling. After stirring under ice cooling for 1 hour and then at room temperature for 1 hour, the insoluble matter (DCU) was removed by filtration, and the solvent was removed from the filtrate under reduced pressure. The residue was dissolved in 40 μl of DMSO, and 185 μl of a phosphate buffer was added thereto. To the resulting mixture was added 825 μl of an aqueous solution of KM-231 antibody (1.0 mg/ml), followed by gentle stirring at 4° C. for 24 hours. After the insoluble matter was removed with a filter (0.45 μm), the antibody fraction was purified by gel filtration HPLC and concentrated in the same manner as in Example 1 to give 660 μg of KM-231-(PEG-Gly-Pro-DNR)$_m$ (protein content: 1.1 mg/ml) (yield: 80%).

In the obtained conjugate, the number of molecules of daunorubicin bound was 1.5 per antibody molecule as calculated from the absorbances at 280 nm and 495 nm in the same manner as in Example 4. It was confirmed that the affinity of the conjugate was approximately equal to that of an unbound antibody according to the fluorescent antibody method described in Example 5.

EXAMPLE 7
Toxin Conjugate (Ia-7): NL-1-[PEG-Ala-Val-Compound (20)]$_m$

In 500 μl of methylene chloride was dissolved 100 μg (0.08 μmol) of Compound (XI-7) obtained in Reference Example 12, and 10 μl of a solution of HONSu (0.41 μmol) in methylene chloride (4.7 mg/ml) and 10 μl of a solution of DCC (0.41 μmol) in methylene chloride (8.4 mg/ml) were added successively thereto under ice cooling. After stirring under ice cooling for 1 hour and then at room temperature for 1.5 hours, the insoluble matter (DCU) was removed by filtration, and the solvent was removed from the filtrate under reduced pressure. The residue was dissolved in 30 μl of DMSO, and 527 μl of a phosphate buffer was added thereto. To the resulting mixture was added 203 μl of an aqueous solution of NL-1 antibody (3.0 mg/ml), followed by gentle stirring at 4° C. for 24 hours. After the insoluble matter was removed with a filter (0.45 μm), the antibody fraction was purified by gel filtration HPLC and concentrated in the same manner as in Example 1 to give 648 μg of NL-1-[PEG-Ala-Val-Compound (20)]$_m$ (protein content: 1.1 mg/ml) (yield: 100%).

It was confirmed that the affinity of the conjugate was approximately equal to that of an unbound antibody according to the fluorescent antibody method described in Example 1.

The number of molecules of Compound (20) bound per antibody molecule was calculated by subjecting the conjugate to enzyme treatment (thermolysin), and quantitatively determining released H-Val-Compound (20) by HPLC according to the method described in Reference Example 27. It was found that in the obtained conjugate, the number of molecules of Compound (20) was 0.38 per antibody molecule.

EXAMPLE 8
Toxin Conjugate (Ia-8): NL-1-[PEG-Ala-Pro-Compound (20)]$_m$

In 500 μl of methylene chloride was dissolved 211 μg (0.17 μmol) of Compound (XI-8) obtained in Reference Example 13, and 10 μl of a solution of HONSu (0.85 μmol) in methylene chloride (9.8 mg/ml) and 10 μl of a solution of DCC (0.85 μmol) in methylene chloride (17.5 mg/ml) were added successively thereto under ice cooling. After stirring under ice cooling for 1 hour and then at room temperature for 1 hour, the insoluble matter (DCU) was removed by filtration, and the solvent was removed from the filtrate under reduced pressure. The residue was dissolved in 60 μl of DMSO, and 1115 μl of a phosphate buffer was added thereto. To the resulting mixture was added 425 μl of an aqueous solution of NL-1 antibody (3.0 mg/ml), followed by gentle stirring at 4° C. for 24 hours. After the insoluble matter was removed with a filter (0.45 μm), the antibody fraction was purified by gel filtration HPLC and concentrated in the same manner as in Example 1 to give 1.2 mg of NL-1-[PEG-Ala-Pro-Compound (20)]$_m$ (protein content: 1.76 mg/ml) (yield: 97%).

It was confirmed that the affinity of the conjugate was approximately equal to that of an unbound antibody according to the fluorescent antibody method described in Example 1.

The number of molecules of Compound (20) bound per antibody molecule was calculated by subjecting the conjugate to enzyme treatment (proline endopeptidase), and quantitatively determining released Compound (20) by HPLC according to the method described in Reference Example 27. It was found that in the obtained conjugate, the number of molecules of Compound (20) was 0.45 per antibody molecule.

EXAMPLE 9
Toxin Conjugate (Ia-9): NL-1-[PEG-Gly-Pro-Compound (20)]$_m$

In 500 μl of methylene chloride was dissolved 135 μg (0.11 μmol) of Compound (XI-9) obtained in Reference Example 14, and 10 μl of a solution of HONSu (0.55 μmol) in methylene chloride (6.3 mg/ml) and 10 μl of a solution of DCC (0.55 μmol) in methylene chloride (11.3 mg/ml) were added successively thereto under ice cooling. After stirring under ice cooling for 1 hour and then at room temperature for 1 hour, the insoluble matter (DCU) was removed by filtration, and the solvent was removed from the filtrate under reduced pressure. The residue was dissolved in 40 μl of DMSO, and 735 μl of a phosphate buffer was added thereto. To the resulting mixture was added 275 μl of an aqueous solution of NL-1 antibody (3.0 mg/ml), followed by gentle stirring at 4° C. for 24 hours. After the insoluble matter was removed with a filter (0.45 μm), the antibody fraction was purified by gel filtration HPLC and concentrated in the same manner as in Example 1 to give 774 μg of NL-1-[PEG-Gly-Pro-Compound (20)]$_m$ (protein content: 1.2 mg/ml) (yield: 94%).

It was confirmed that the affinity of the conjugate was approximately equal to that of an unbound antibody according to the fluorescent antibody method described in Example 1.

The number of molecules of Compound (20) bound per antibody molecule was calculated by subjecting the conjugate to enzyme treatment (proline endopeptidase), and quantitatively determining released Compound (20) by HPLC according to the method described in Reference Example 27. It was found that in the obtained conjugate, the number of molecules of Compound (20) was 0.49 per antibody molecule.

EXAMPLE 10
Toxin Conjugate (Ia-10): KM-231-[PEG-Ala-Val-Compound (12)]$_m$

In 0.4 ml of methanol was dissolved 0.45 mg (0.33 μmol) of Compound (X-1) obtained in Reference Example 16, and 1 mg of 10% palladium carbon catalyst was added thereto in an atmosphere of nitrogen, followed by vigorous stirring in a hydrogen stream at −15° C. for 5 hours. After removal of the catalyst by filtration, the solvent was removed from the filtrate under reduced pressure at a temperature below 0° C. to obtain 0.14 mg (0.11 μmol) of HO-PEG-Ala-Val-Compound (12). The obtained compound (0.14 mg) was dissolved in 250 μl of a solution of HONSu in methylene chloride (0.076 mg/ml) under ice cooling, and 250 μl of a solution of DCC in methylene chloride (0.14 mg/ml) was added thereto, followed by stirring for 2.5 hours under ice cooling. The insoluble matter (DCU) was removed by filtration, and the solvent was removed from the filtrate under reduced pressure at a temperature below 0° C. The residue was dissolved in 36 μl of DMSO, and 204 μl of an ice-cooled phosphate buffer was added thereto. To the resulting mixture was added 0.56 ml of an aqueous solution of KM-231 antibody (0.99 mg/ml) under ice cooling, followed by gentle stirring at 4° C. for 24 hours. After the insoluble matter was removed with a filter (0.22 μm), the antibody fraction was purified by gel filtration HPLC and concentrated in the same manner as in Example 1 to give 250 μg of KM-231-[PEG-Ala-Val-Compound (12)]$_m$ (protein content: 0.5 mg/ml) (yield: 5.1%).

It was confirmed that the affinity of the conjugate was approximately equal to that of an unbound antibody according to the fluorescent antibody method described in Example 4.

EXAMPLE 11

Toxin Conjugate (Ia-11): KM-641-[PEG-Ala-Val-Compound (12)]$_m$

In 0.3 ml of methanol was dissolved 2.5 mg (1.8 μmol) of Compound (X-1) obtained in Reference Example 16, and 1 mg of 10% palladium carbon catalyst was added thereto in an atmosphere of nitrogen, followed by vigorous stirring in a hydrogen stream at −18° C. for 4 hours. After removal of the catalyst by filtration, the solvent was removed from the filtrate under reduced pressure at a temperature below 0° C. to obtain 0.05 mg (0.04 μmol) of HO-PEG-Ala-Val-Compound (12). The obtained compound (0.05 mg) was dissolved in 250 μl of a solution of HONSu in methylene chloride (0.028 mg/ml) under ice cooling, and 250 μl of a solution of DCC in methylene chloride (0.05 mg/ml) was added thereto, followed by stirring for 4.5 hours under ice cooling. The insoluble matter (DCU) was removed by filtration, and the solvent was removed from the filtrate under reduced pressure at a temperature below 0° C. The residue was dissolved in 15 μl of DMSO, and 80 μl of a cooled phosphate buffer was added thereto. To the resulting mixture was added 205 μl of an aqueous solution of KM-641 antibody (1.47 mg/ml) under ice cooling, followed by gentle stirring at 4° C. for 24 hours. After the insoluble matter was removed with a filter (0.22 μm), the antibody fraction was purified by gel filtration HPLC and concentrated in the same manner as in Example 1 to give 200 μg of KM-641-[PEG-Ala-Val-Compound (12)]$_m$ (protein content: 70 μg/ml) (yield: 66%).

It was confirmed that the affinity of the conjugate was approximately equal to that of an unbound antibody according to the fluorescent antibody method described in Example 4.

REFERENCE EXAMPLE 1

Compound (VIII-1): BzlO-PEG-Ala-Val-OH (a) Compound (V-1): BzlO-PEG-OH

In 100 ml of DMF was dissolved 10 g (16.7 mmol) of polyethylene glycol dicarboxylic acid [HO-PEG-OH, average molecular weight: 600 (Fluka Fine Chemicals Co.)], and 2.75 g of anhydrous potassium carbonate was added thereto, followed by stirring at room temperature. To the resulting solution was added dropwise a solution prepared by dissolving 2 ml (8.4 mmol) of benzyl bromide in 100 ml of DMF, over 30 minutes, followed by further stirring for 24 hours. To the resulting solution was added 100 ml of water, and the mixture was adjusted to pH 1–2 with iN HCl. After extraction was carried out six times with 100 ml portions of ethyl acetate, the ethyl acetate layer was dried over anhydrous sodium sulfate, and the solvent was removed under reduced pressure. Then, the residue was subjected to purification using 200 ml of silica gel (Wako Gel C-200), and as the developer, 200 ml each of chloroform-methanol mixtures (100:0, 50:1, 30:1, 20:1, 10:1, 5:1). The eluate was taken in 10 ml fractions. The solvent was removed from the desired fractions under reduced pressure, the desired fractions being identified by silica gel thin layer chromatography. The residue was dissolved in a small amount of chloroform, followed by filtration. The solvent was removed from the filtrate under reduced pressure to give 0.9 g (1.3 mmol) of the desired compound, BzlO-PEG-OH (yield: 7.8%).

Silica gel thin layer chromatography: Kieselgel 60 (Merck & Co., Inc.) Chloroform:methanol=3:1; Rf value: 0.5; $^1$HNMR spectrum (100 MHz, in CDCl$_3$) δ (ppm): 7.36 (5H, m, C$_6$H$_5$), 5.19 (2H, s, CH$_2$), 4.12 (4H, s, OCH$_2$), 3.64 (4nH, brs, OCH$_2$CH$_2$)

(b) Compound (VI-1): H-Ala-Val-OtBu

In 160 ml of THF was dissolved 1.6 g (7.6 mmol) of H-Val-OtBu hydrochloride, and 1.0 ml (9.2 mmol) of NMM was added thereto, followed by stirring at room temperature. To the resulting solution was added 2.5 g (7.6 mmol) of Z-Ala-ONSu, followed by further stirring at room temperature for 24 hours. After removal of the solvent under reduced pressure, 50 ml each of chloroform and a phosphate buffer (pH 7.0) were successively added. The chloroform layer was extracted and dried over sodium sulfate, and the solvent was removed under reduced pressure to obtain an oily residue. The obtained residue was subjected to purification using 200 ml of silica gel (Wako Gel C-200), and as the developer, 200 ml each of chloroform-methanol mixtures (100:0, 100:1, 50:1). The eluate was taken in 10 ml fractions. The solvent was removed from the desired fractions under reduced pressure, the desired fractions being identified by silica gel thin layer chromatography [Kieselgel 60 (Merck & Co., Inc.), chloroform:methanol=10:1, Rf value: 0.9], whereby 3.0 g of Z-Ala-Val-OtBu was obtained as an oily substance. The obtained compound (3.0 g) was dissolved in 60 ml of THF and 60 ml of methanol, and 320 mg of 10% palladium carbon catalyst was added thereto, followed by vigorous stirring in an atmosphere of hydrogen at room temperature for 7 hours. The catalyst was removed by filtration, and the solvent was removed from the filtrate under reduced pressure to give 1.7 g (7.1 mmol) of the desired compound, H-Ala-Val-OtBu (yield: 93%).

Silica gel thin layer chromatography: Kieselgel 60 (Merck & Co., Inc.) Chloroform:methanol=10:1; Rf value: 0.4; Mass spectrum (SIMS): 245 (M+H)

(c) Compound (VIII-1): BzlO-PEG-Ala-Val-OH

In 6.0 ml of methylene chloride was dissolved 400 mg (0.58 mmol) of BzlO-PEG-OH obtained in the above (a), and 119 mg (0.58 mmol) of DCC was added thereto under ice cooling, followed by stirring for 20 minutes. To the resulting solution was added 6.0 ml of a solution of 118 mg (0.48 mmol) of H-Ala-Val-OtBu obtained in the above (b) in methylene chloride, followed by further stirring under ice cooling for 2 hours. After removal of the solvent under reduced pressure, 5.0 ml of ethyl acetate was added, followed by stirring under ice cooling for one hour. The insoluble matter (DCU) was removed by filtration, and the solvent was removed from the filtrate under reduced pressure. Then the residue was subjected to purification using 50 ml of silica gel, and as the developer, 100 ml each of chloroform-methanol mixtures (100:0, 100:1, 50:1). The eluate was taken in 5 ml fractions. The solvent was removed from the desired fractions under reduced pressure, the desired fractions being identified by silica gel thin layer chromatography [Kieselgel 60 (Merck & Co., Inc.), chloroform:methanol=10:1, Rf value: 0.7], whereby 0.19 g of BzlO-PEG-Ala-Val-OtBu was obtained. In 4.6 ml of methylene chloride was dissolved 0.19 g of the obtained compound, and 4.6 ml of TFA was added thereto, followed by stirring at room temperature for 24 hours. After removal of the solvent under reduced pressure, the residue was subjected to purification using 20 ml of silica gel, and as the developer, 50 ml each of chloroform-methanol mixtures (100:0, 100:1, 50:1, 30:1, 10:1, 5:1). The eluate was taken in 5 ml fractions. The solvent was removed from the desired fractions under reduced pressure, the desired fractions being identified by silica gel thin layer chromatography, whereby 0.14 g (0.16 mmol) of the desired compound, BzlO-PEG-Ala-Val-OH, was obtained (yield: 28%).

Silica gel thin layer chromatography: Kieselgel 60 (Merck & Co., Inc.) Chloroform:methanol=10:1; Rf value: 0.2; $^1$HNMR spectrum (100 MHz, in $CDCl_3$) δ (ppm): 7.36 (5H, m, $C_6H_5$), 5.19 (2H, s, $CH_2$), 4.12 (4H, s, $OCH_2$), 3.64 (4nH, brs, $OCH_2CH_2$), 3.23 [1H, s, CH(Ala)], 2.23 [1H, brq, J=6.0 Hz, CH(Val)], 1.26 [1H, br, CH(Val)], 1.17 [3H, d, J=2.8 Hz, $CH_3$(Ala)], 0.89 [6H, brd, J=2.5 Hz, $CH_3$(Val)]

REFERENCE EXAMPLE 2

Compound (VIII-2): BzlO-PEG-Ala-Pro-OH (a) Compound (VI-2): H-Ala-Pro-OtBu

In 65.7 ml of THF was dissolved 657 mg (3.8 mmol) of H-Pro-OtBu, and 1.23 g (3.8 mmol) of Z-Ala-ONSu was added thereto, followed by stirring at room temperature for 24 hours. After removal of the solvent under reduced pressure, 50 ml each of chloroform and a phosphate buffer (pH 7.0) were successively added. The chloroform layer was extracted and dried over anhydrous sodium sulfate, and the solvent was removed under reduced pressure to obtain an oily residue. The obtained residue was purified using 200 ml of silica gel (Wako Gel C-200), and as the developer, 100 ml each of chloroform-methanol mixtures (100:0, 100:1, 50:1). The solvent was removed from the desired fractions under reduced pressure, the desired fractions being identified by silica gel thin layer chromatography [Kieselgel 60 (Merck & Co., Inc.), chloroform:methanol=10:1, Rf value: 0.8], whereby 1.47 g of Z-Ala-Pro-OtBu was obtained as an oily substance. The obtained compound (1.47 g) was dissolved in 30 ml of THF and 30 ml of methanol, and 250 mg of 10% palladium carbon catalyst was added thereto, followed by vigorous stirring in an atmosphere of hydrogen at room temperature for 8 hours. After the catalyst was removed by filtration, the solvent was removed from the filtrate under reduced pressure. Then the residue was subjected to purification using 200 ml of silica gel (Wako Gel C-200), and as the developer, 100 ml each of chloroform-methanol mixtures (100:0, 100:1, 50:1, 30:1, 10:1, 5:1). The eluate was taken in 10 ml fractions. The solvent was removed from the desired fractions under reduced pressure, the desired fractions being identified by silica gel thin layer chromatography, whereby 0.67 g (2.8 mmol) of the desired compound, H-Ala-Pro-OtBu, was obtained (yield: 74%).

Silica gel thin layer chromatography: Kieselgel 60 (Merck & Co., Inc.); Chloroform:methanol=10:1; Rf value: 0.2; Mass spectrum (SIMS): 243 (M+H)

(b) Compound (VIII-2): BzlO-PEG-Ala-Pro-OH

In 6.0 ml of methylene chloride was dissolved 400 mg (0.58 mmol) of BzlO-PEG-OH obtained in Reference Example 1 (a), and 119 mg (0.58 mmol) of DCC was added thereto under ice cooling, followed by stirring for 20 minutes. To the resulting solution was added 6.0 ml of a solution of 116 mg (0.48 mmol) of H-Ala-Pro-OtBu obtained in the above (a) in methylene chloride, followed by further stirring under ice cooling for 2 hours. After removal of the solvent under reduced pressure, 5.0 ml of ethyl acetate was added, followed by stirring under ice cooling for one hour. The insoluble matter (DCU) was removed by filtration, and the solvent was removed from the filtrate under reduced pressure to obtain 0.21 g of a residue containing BzlO-PEG-Ala-Pro-OtBu. The obtained residue was dissolved in 5.1 ml of methylene chloride, and 5.1 ml of TFA was added thereto, followed by stirring at room temperature for 24 hours. After removal of the solvent under reduced pressure, the residue was subjected to purification using 20 ml of silica gel (Wako Gel C-200), and as the developer, 50 ml each of chloroform-methanol mixtures (100:0, 100:1, 50:1, 30:1, 10:1, 5:1, 3:1). The eluate was taken in 5 ml fractions. The solvent was removed from the desired fractions under reduced pressure, the desired fractions being identified by silica gel thin layer chromatography, whereby 164 mg (0.19 mmol) of the desired compound, BzlO-PEG-Ala-Pro-OH, was obtained (yield: 33%).

Silica gel thin layer chromatography: Kieselgel 60 (Merck & Co., Inc.); Chloroform:methanol=5:1; Rf value: 0.2; $^1$HNMR spectrum (100 MHz, in $CDCl_3$) δ (ppm): 7.36 (5H, m, $C_6H_5$), 5.19 (2H, s, $CH_2$), 4.40 [2H, br, $CH_2$ (Pro)], 4.12 (4H, s, $OCH_2$), 3.80 [1H, q, J=6.0 Hz, CH(Ala)], 3.64 (4nH, brs, $OCH_2CH_2$), 3.59 [2H, br, $CH_2$(Pro)], 2.36 [1H, br, CH(Pro)], 2.02 [2H, br, $CH_2$(Pro)], 1.29 [3H, brd, J=3.5 Hz, $CH_3$(Ala)]

REFERENCE EXAMPLE 3

Compound (VIII-3): BzlO-PEG-Gly-Pro-OH (a) Compound (VI-3): H-Gly-Pro-OtBu

In 100 ml of THF was dissolved 1.0 g (5.8 mmol) of H-Pro-OtBu, and 1.8 g (5.8 mmol) of Z-Gly-ONSu was added thereto, followed by stirring at room temperature for 24 hours. After removal of the solvent under reduced pressure, 50 ml each of chloroform and a phosphate buffer (pH 7.0) were successively added. The chloroform layer was extracted and dried over anhydrous sodium sulfate, and the solvent was removed under reduced pressure to obtain an oily residue. The obtained residue was subjected to purification using 200 ml of silica gel (Wako Gel C-200), and as the developer, 150 ml each of chloroform-methanol mixtures (100:0, 100:1, 50:1). The eluate was taken in 10 ml fractions. The solvent was removed from the desired fractions under reduced pressure, the desired fractions being identified by silica gel thin layer chromatography [Kieselgel 60 (Merck & Co., Inc.), chloroform:methanol=10:1, Rf value: 0.9], whereby 1.93 g of Z-Gly-Pro-OtBu was obtained as an oily substance. The obtained compound (1.93 g) was dissolved in 20 ml of THF and 40 ml of methanol, and 440 mg of 10% palladium carbon catalyst was added thereto, followed by vigorous stirring in an atmosphere of hydrogen at room temperature for 15 hours. After the catalyst was removed by filtration, the solvent was removed from the filtrate under reduced pressure to give 1.13 g (4.9 mmol) of the desired compound, H-Gly-Pro-OtBu (yield: 86%).

Silica gel thin layer chromatography: Kieselgel 60 (Merck & Co., Inc.); Chloroform:methanol=10:1; Rf value: 0.2; Mass spectrum (SIMS): 211 (M+H)

(b) Compound (VIII-3): BzlO-PEG-Gly-Pro-OH

In 6.0 ml of methylene chloride was dissolved 400 mg (0.58 mmol) of BzlO-PEG-OH obtained in Reference Example 1 (a), and 119 mg of DCC was added thereto under ice cooling, followed by stirring for 20 minutes. To the resulting solution was added 6.0 ml of a solution of 110 mg (0.48 mmol) of H-Gly-Pro-OtBu obtained in the above (a) in methylene chloride, followed by further stirring under ice cooling for 2 hours. After removal of the solvent under reduced pressure, 5.0 ml of ethyl acetate was added, followed by stirring under ice cooling for one hour. The insoluble matter (DCU) was removed by filtration, and the solvent was removed from the filtrate under reduced pressure. Then the residue was subjected to purification using 50 ml of silica gel (Wako Gel C-200), and as the developer, 100 ml each of chloroform-methanol mixtures (100:0, 100:1, 50:1). The eluate was taken in 10 ml fractions. The solvent was removed from the desired fractions under reduced pressure, the desired fractions being identified by silica gel thin layer chromatography [Kieselgel 60 (Merck & Co., Inc.), chloroform:methanol=10:1, Rf value: 0.7], whereby 0.21 g of BzlO-PEG-Gly-Pro-OtBu was obtained. In 5.1 ml of methylene chloride was dissolved 0.21 g of the obtained compound, and 5.1 ml of TFA was added thereto, followed by stirring at room temperature for 24 hours. After removal of the solvent under reduced pressure, the residue was subjected to purification using 20 ml of silica gel (Wako Gel C-200), and as the developer, 50 ml each of chloroform-methanol mixtures (100:0, 100:1, 50:1, 30:1, 20:1, 10:1, 5:1, 3:1). The eluate was taken in 5 ml fractions. The solvent was removed from the desired fractions under reduced pressure, the desired fractions being identified by silica gel thin layer chromatography, whereby 164 mg (0.2 mmol) of the desired compound, BzlO-PEG-Gly-Pro-OH, was obtained (yield: 33%).

Silica gel thin layer chromatography: Kieselgel 60 (Merck & Co., Inc.); Chloroform:methanol=10:1; Rf value: 0.2; $^1$HNMR spectrum (100 MHz, in CDCl$_3$) δ (ppm): 7.36 (5H, m, C$_6$H$_5$), 5.19 (2H, s, CH$_2$), 4.40 [2H, br, CH$_2$(Pro)], 4.12 (4H, s, OCH$_2$), 3.82 [2H, s, CH$_2$(Gly)], 3.64 (4nH, brs, OCH$_2$CH$_2$), 3.59 [2H, br, CH$_2$(Pro)], 2.21 [1H, s, CH(Pro)], 2.02 [2H, br, CH$_2$(Pro)]

REFERENCE EXAMPLE 4

Compound (VIII-4): PicO-PEG-Gly-Pro-OH (a) Compound (V-2): PicO-PEG-OH

In 50 ml of DMF was dissolved 10 g (16.7 mmol) of HO-PEG-OH, and 1.37 g (8.4 mmol) of picolyl chloride hydrochloride and 3.4 ml (25.1 mmol) of triethylamine were successively added thereto, followed by stirring at 90 to 100° C. for 2 hours. Then, the solvent was removed under reduced pressure to obtain a mixture of polyethylene glycol dicarboxylic acid (unreacted), monopicolyl ester and dipicolyl ester. In 100 ml of chloroform was dissolved 1.97 g of this reaction mixture, and 100 ml of water was added thereto, followed by addition of 1N sodium hydroxide to adjust the water layer to pH 9.5. After the water layer was extracted and adjusted to pH 6.5 with 1N HCl, extraction was carried out 6 to 7 times with 100 ml portions of chloroform. During the repeated extractions, the pH of the water layer was kept at 6.5 with 1N HCl. After the chloroform layer was dried over anhydrous sodium sulfate, the solvent was removed under reduced pressure to give 1.0 g (1.5 mmol) of the desired compound, PicO-PEG-OH (yield: 8.9%).

Silica gel thin layer chromatography: Kieselgel 60 (Merck & Co., Inc.); Chloroform:methanol=3:1; Rf value: 0.5; $^1$HNMR spectrum (100 MHz, in CDCl$_3$) δ (ppm): 5.21 (2H, s, CH$_2$), 4.12 (4H, s, OCH$_2$), 3.64 (4nH, brs, OCH$_2$CH$_2$), 7.28 [2H, d, J=3.5 Hz, H-3, H-5(Pic)], 8.65 [2H, d, J=3.5 Hz, H-2, H-6(Pic)]

(b) Compound (VIII-4): PicO-PEG-Gly-Pro-OH

In 8 ml of methylene chloride was dissolved 500 mg (0.73 mmol) of PicO-PEG-OH obtained in the above (a), and 151 mg (0.73 mmol) of DCC was added thereto under ice cooling, followed by stirring for 20 minutes. To the resulting solution was added 8 ml of a solution of 139 mg (0.61 mmol) of H-Gly-Pro-OtBu obtained in Reference Example 3 (a) in methylene chloride, followed by stirring under ice cooling for 3 hours. After removal of the solvent under reduced pressure, 5 ml of ethyl acetate was added, followed by stirring under ice cooling for one hour. The insoluble matter (DCU) was removed by filtration, and the solvent was removed from the filtrate under reduced pressure. Then the residue was subjected to purification using 50 ml of silica gel (Wako Gel C-200), and as the developer, 50 ml each of chloroform-methanol mixtures (100:0, 100:1, 50:1, 30:1, 20:1, 10:1). The eluate was taken in 5 ml fractions. The solvent was removed from the desired fractions under reduced pressure, the desired fractions being identified by silica gel thin layer chromatography [Kieselgel 60 (Merck & Co., Inc.), chloroform:methanol=10:1, Rf value: 0.5], whereby 374 mg of PicO-PEG-Gly-Pro-OtBu was obtained. In 9.0 ml of methylene chloride was dissolved 374 mg of the obtained compound, and 9.0 ml of TFA was added thereto, followed by stirring at room temperature for 24 hours. After removal of the solvent under reduced pressure, the residue was subjected to purification using 20 ml of silica gel (Wako Gel C-200), and as the developer, 50 ml each of chloroform-methanol mixtures (100:0, 100:1, 50:1, 30:1, 10:1, 5:1). The eluate was taken in 5 ml fractions. The solvent was removed from the desired fractions under reduced pressure, the desired fractions being identified by silica gel thin layer chromatography, whereby 131 mg (0.16 mmol) of the desired compound, PicO-PEG-Gly-Pro-OH, was obtained (yield: 26%)

Silica gel thin layer chromatography: Kieselgel 60 (Merck & Co., Inc.); Chloroform:methanol=5:1; Rf value: 0.1; $^1$HNMR spectrum (100 MHz, in CDCl$_3$) δ (ppm): 5.21 (2H, s, CH$_2$), 4.40 [2H, br, CH$_2$(Pro)], 4.12 (4H, s, OCH$_2$), 3.82 [2H, s, CH$_2$(Gly)], 3.64 (4nH, brs, OCH$_2$CH$_2$), 3.59 [2H, br, CH$_2$(Pro)], 2.21 [1H, s, CH(Pro)], 2.02 [2H, br, CH$_2$(Pro)], 7.28 [2H, d, J=3.5 Hz, H-3, H-5(Pic)], 8.65 [2H, d, J=3.5 Hz, H-2, H-6(Pic)]

REFERENCE EXAMPLE 5

Compound (VIII-5): PicO-PEG-Ala-Val-OH

In 7 ml of methylene chloride was dissolved 459 mg (0.67 mmol) of PicO-PEG-OH obtained in Reference Example 4 (a), and 138 mg (0.80 mmol) of DCC was added thereto under ice cooling, followed by stirring for 20 minutes. To the resulting solution was added 7 ml of a solution of 134 mg (0.55 mmol) of H-Ala-Val-OtBu obtained in Reference Example 1 (b) in methylene chloride, followed by further stirring under ice cooling for 3 hours. After removal of the solvent under reduced pressure, 5 ml of ethyl acetate was added, followed by stirring under ice cooling for one hour. The insoluble matter (DCU) was removed by filtration, and the solvent was removed from the filtrate under reduced pressure. Then the residue was subjected to purification using 50 ml of silica gel (Wako Gel C-200), and as the developer, 50 ml each of chloroform-methanol mixtures (100:0, 100:1, 50:1, 30:1, 20:1). The eluate was taken in 5 ml fractions. The solvent was removed from the desired fractions under reduced pressure, the desired fractions being identified by silica gel thin layer chromatography [Kieselgel 60 (Merck & Co., Inc.), chloroform:methanol=10:1, Rf value: 0.4], whereby 328 mg of PicO-PEG-Ala-Val-OtBu was obtained. In 8.0 ml of methylene chloride was dissolved 328 mg of the obtained compound, and 8.0 ml of TFA was added thereto, followed by stirring at room temperature for 24 hours. After removal of the solvent under reduced pressure, the residue was subjected to purification using 20 ml of silica gel (Wako Gel C-200), and as the developer, 50 ml each of chloroform-methanol mixtures (100:0, 100:1, 50:1, 30:1, 10:1, 5:1). The eluate was taken in 5 ml fractions. The solvent was removed from the desired fractions under reduced pressure, the desired fractions being identified by silica gel thin layer chromatography, whereby 131 mg (0.15 mmol) of the desired compound, PicO-PEG-Gly-Pro-OH, was obtained (yield: 27%).

Silica gel thin layer chromatography: Kieselgel 60 (Merck & Co., Inc.); Chloroform:methanol=5:1; Rf value: 0.1; $^1$HNMR spectrum (100 MHz, in CDCl$_3$) δ (ppm): 5.21 (2H, s, CH$_2$), 4.12 (4H, s, OCH$_2$), 3.64 (4nH, brs, OCH$_2$CH$_2$), 3.23 [1H, s, CH(Ala)], 2.23 [1H, brq, J=6.0 Hz, CH(Val)], 7.28 [2H, d, J=3.5 Hz, H-3, H-5(Pic)], 1.26 [1H, s, CH(Val)], 1.17 [3H, d, J=2.8 Hz, CH$_3$(Ala)], 8.65 [2H, d, J=3.5 Hz, H-2, H-6(Pic)], 0.89 [6H, q, J=2.5 Hz, CH$_3$(Val)]

REFERENCE EXAMPLE 6
Compound (XI-1): HO-PEG-Ala-Val-ADM

In 0.5 ml of methylene chloride was dissolved 11.4 mg (13.3 µmol) of Compound (VIII-1) obtained in Reference Example 1, and 3.4 mg (29.5 µmol) of HONSu and 6.2 mg (30.1 µmol) of DCC were added thereto under ice cooling, followed by stirring at 0° C. for 2 hours. The insoluble matter (DCU) was removed by filtration, and the solvent was removed from the filtrate under reduced pressure. Then the residue was dissolved in 300 µl of methanol in a stream of nitrogen, and 2–3 mg of 10% palladium carbon catalyst was added thereto, followed by vigorous stirring in a stream of hydrogen at room temperature for 2 hours. After removal of the catalyst by filtration, the solvent was removed from the filtrate under reduced pressure. To the residue was added under ice cooling a solution prepared by dissolving 0.25 mg (0.46 µmol) of adriamycin hydrochloride in 383 µl of a solution of triethylamine in dry DMF (8.5 µg/ml). After the resulting mixture was allowed to stand under ice cooling for 30 minutes, the solvent was removed under reduced pressure. The residue was subjected to purification using 3.0 ml of silica gel (Wako Gel C-200). The by-product, BzlO-PEG-Ala-Val-ADM, was removed by elution using, as the developer, 10 ml each of chloroform-methanol mixtures (10:1, 7:1, 5:1, 3:1, 2:1). Then, the desired HO-PEG-Ala-Val-ADM was eluted with 20 ml of a mixture of chloroform:methanol:water (13:6:1). The solvent was removed from the desired fraction under reduced pressure to give 179 µg (0.20 µmol) of HO-PEG-Ala-Val-ADM (yield from adriamycin: 44%).

Silica gel thin layer chromatography: Kieselgel 60 (Merck & Co., Inc.); Chloroform:methanol:water=13:6:1; Rf value: 0.6; $^1$HNMR spectrum (500 MHz, in CDCl$_3$) δ (ppm): PEG-Ala-Val moiety 4.19 (4H, s, OCH$_2$), 3.48 (4nH, brs, OCH$_2$CH$_2$), 3.22 [1H, brs, CH(Ala)], 2.23 [1H, brq, J=6.0 Hz, CH(Val)], 1.25 [1H, s, CH(Val)], 1.17 [3H, d, J=2.8 Hz, CH$_3$(Ala)], 0.89 [6H, brm, CH$_3$(Val)], Adriamycin moiety 7.99 (2H, d, J=6.0 Hz, H-1, H-2), 7.73 (1H, brm, H-3), 5.43 (1H, brm, H-1'), 5.42 (1H, d, J=3.7 Hz, H-14b), 5.35 (1H, d, J=3.7 Hz, H-1'), 5.14 (1H, brs, H-7), 4.34 (1H, q, J=6.5 Hz, H-5'), 4.10 (3H, s, 4-OCH$_3$), 3.22 (1H, d, J=18 Hz, H-10b), 3.10 (1H, d, J=18 Hz, H-10a), 2.50 (1H, brd, J=14 Hz, H-8b), 2.23 (1H, d, J=14 Hz, H-8a), 2.06 (1H, brm, H-2'b), 1.89 (1H, brm, H-2'a), 1.28 (3H, d, J=6.5 Hz, 5'-CH$_3$); Ultraviolet absorption spectrum (in methanol, $\lambda_{max}$): 232, 274, 495, 534, 575 nm; Infrared absorption spectrum (in chloroform): 3580, 3400, 3000, 2924, 2870, 1786, 1717, 1660, 1605, 1520, 1450, 1295, 1105 cm$^{-1}$ REFERENCE EXAMPLE 7
Compound (XI-2): HO-PEG-Ala-Pro-ADM In 0.5 ml of methylene chloride was dissolved 9.5 mg (11.1 µmol) of Compound (VIII-2) obtained in Reference Example 2, and 3.4 mg (29.5 µmol) of HONSu and 6.2 mg (30.1 µmol) of DCC were added thereto under ice cooling, followed by stirring at 0° C. for 2 hours. The insoluble matter (DCU) was removed by filtration, and the solvent was removed from the filtrate under reduced pressure. Then the residue was dissolved in 300 µl of methanol in a stream of nitrogen, and 2–3 mg of 10% palladium carbon catalyst was added thereto, followed by vigorous stirring in a stream of hydrogen at room temperature for 2 hours. After removal of the catalyst by filtration, the solvent was removed from the filtrate under reduced pressure. To the residue was added under ice cooling a solution prepared by dissolving 0.25 mg (0.46 µmol) of adriamycin hydrochloride in 383 µl of a solution of triethylamine in dry DMF (8.5 µg/ml). After the resulting mixture was allowed to stand under ice cooling for 30 minutes, the solvent was removed under reduced pressure. The residue was subjected to purification using 3.0 ml of silica gel (Wako Gel C-200). The by-product, BzlO-PEG-Ala-Pro-ADM, was removed by elution using, as the developer, 10 ml each of chloroform-methanol mixtures (10:1, 7:1, 5:1, 3:1, 2:1). Then, the desired HO-PEG-Ala-Pro-ADM was eluted with 20 ml of a mixture of chloroform:methanol:water (13:6:1). The solvent was removed from the desired fraction under reduced pressure to give 182 µg (0.21 µmol) of HO-PEG-Ala-Pro-ADM (yield from adriamycin: 46%).

Silica gel thin layer chromatography: Kieselgel 60 (Merck & Co., Inc.); Chloroform:methanol:water=13:6:1; Rf value: 0.6; $^1$HNMR spectrum (500 MHz, in CDCl$_3$) δ (ppm): PEG-Ala-Pro moiety 4.52 [2H, brm, CH$_2$(Pro)], 4.12 (4H, s, OCH$_2$), 3.75 [1H, q, J=6.0 Hz, CH(Ala)], 3.64 (4nH, brs, OCH$_2$CH$_2$), 3.55 [2H, br, CH$_2$(Pro)], 2.34 [1H, br, CH(Pro)], 2.04 [2H, brm, CH$_2$(Pro)], 1.15 [3H, br, CH$_3$(Ala)], Adriamycin moiety 8.06 (2H, d, J=6.0 Hz, H-1, H-2), 7.80 (1H, brm, H-3), 5.54 (1H, brm, H-1'), 5.51 (1H, d, J=3.5 Hz, H-14b), 5.29 (1H, d, J=3.5 Hz, H-14a), 5.19 (1H, brs, H-7), 4.31 (1H, t, J=6.5 Hz, H-5'), 4.13 (3H, s, 4-OCH$_3$), 3.41 (1H, d, J=18 Hz, H-10b), 3.07 (1H, d, J=18 Hz, H-10a), 2.59 (1H, brd, J=14 Hz, H-8b), 2.27 (1H, d, J=14 Hz, H-8a), 2.14 (1H, br, H-2'b), 1.82 (1H, br, H-2'a), 1.26 (3H, d, J=6.5 Hz, 5'—CH$_3$); Ultraviolet absorption spectrum (in methanol, $\lambda_{max}$): 233, 252, 290, 470, 495, 534, 578 nm; Infrared absorption spectrum (in chloroform): 3580, 3400, 3005, 2930, 2870, 1780, 1718, 1658, 1580, 1450, 1282, 1110 cm$^{-1}$ REFERENCE EXAMPLE 8
Compound (XI-3): HO-PEG-Gly-Pro-ADM In 0.5 ml of methylene chloride was dissolved 10.8 mg (12.5 µmol) of Compound (VIII-3) obtained in Reference Example 3, and 3.4 mg (29.5 µmol) of HONSu and 6.2 mg (30.1 µmol) of DCC were added thereto under ice cooling, followed by stirring at 0° C. for 2 hours. The insoluble matter (DCU) was removed by filtration, and the solvent was removed from the filtrate under reduced pressure. Then the residue was dissolved in 300 µl of methanol in a stream of nitrogen, and 2–3 mg of 10% palladium carbon catalyst was added thereto, followed by vigorous stirring in a stream of hydrogen at room temperature for 2 hours. After removal of the catalyst by filtration, the solvent was removed from the filtrate under reduced pressure. To the residue was added under ice cooling a solution prepared by dissolving 0.175 mg (0.3 μmol) of adriamycin hydrochloride in 250 μl of a solution of triethylamine in dry DMF (8.5 μg/ml). After the resulting mixture was allowed to stand under ice cooling for 30 minutes, the solvent was removed under reduced pressure. The residue was subjected to purification using 5.0 ml of silica gel (Wako Gel C-200). The by-product, BzlO-PEG-Gly-Pro-ADM, was removed by elution using, as the developer, 10 ml each of chloroform-methanol mixtures (5:1, 3:1, 2:1). Then, the desired HO-PEG-Gly-Pro-ADM was eluted with 20 ml of a mixture of chloroform:methanol:water (13:6:1). The solvent was removed from the desired fraction under reduced pressure to give 240 μg (0.19 μmol) of HO-PEG-Gly-Pro-ADM (yield from adriamycin: 62%).

Silica gel thin layer chromatography: Kieselgel 60 (Merck & Co., Inc.); Chloroform:methanol:water=13:6:1; Rf value: 0.6; $^1$HNMR spectrum (500 MHz, in CDCl$_3$) δ (ppm): PEG-Gly-Pro moiety 4.22 [2H, brm, CH$_2$(Pro)], 4.17 (4H, m, OCH$_2$), 4.08 [2H, s, CH$_2$(Gly)], 3.64 (4nH, brs, OCH$_2$CH$_2$), 3.52 [2H, br, CH$_2$(Pro)], 2.22 [1H, br, CH(Pro)], 1.95 [2H, brm, CH$_2$(Pro)], Adriamycin moiety 8.05 (2H, m, H-1, H-2), 7.77 (1H, m, H-3), 5.50 (1H, d, J=3.7 Hz, H-1'), 5.34 (1H, d, J=3.5 Hz, H-14b), 5.30 (1H, d, J=3.8 Hz, H-1'), 5.19 (1H, brs, H-7), 4.31 (1H, q, J=6.8 Hz, H-5'), 4.10 (3H, s, 4-OCH$_3$), 3.30 (1H, d, J=18 Hz, H-10b), 3.03 (1H, d, J=18 Hz, H-10a), 2.48 (1H, brd, J=14 Hz, H-8b), 2.20 (1H, d, J=14 Hz, H-8a), 2.04 (1H, brm, H-2'b), 1.83 (1H, m, H-2'a), 1.14 (3H, brd, J=7 Hz, 5'—CH$_3$); Ultraviolet absorption spectrum (in methanol, λ$_{max}$): 233, 250, 290, 470, 495, 530, 576 nm; Infrared absorption spectrum (in chloroform): 3590, 3400, 3000, 2940, 2860, 1720, 1650, 1450, 1115 cm$^{-1}$ REFERENCE EXAMPLE 9
Compound (XI-4): HO-PEG-Ala-Val-DNR In 0.5 ml of methylene chloride was dissolved 11.4 mg (13.3 μmol) of Compound (VIII-1) obtained in Reference Example 1, and 3.6 mg (31.3 μmol) of HONSu and 6.4 mg (31.0 μmol) of DCC were added thereto under ice cooling, followed by stirring at 0° C. for 2 hours. The insoluble matter (DCU) was removed by filtration, and the solvent was removed from the filtrate under reduced pressure. Then the residue was dissolved in 300 μl of methanol in a stream of nitrogen, and 2–3 mg of 10% palladium carbon catalyst was added thereto, followed by vigorous stirring in a stream of hydrogen at room temperature for 2 hours. After removal of the catalyst by filtration, the solvent was removed from the filtrate under reduced pressure. To the residue was added under ice cooling a solution prepared by dissolving 0.90 mg (1.7 μmol) of daunorubicin hydrochloride in 500 μl of a solution of triethylamine in dry DMF (0.48 μg/ml). After the resulting mixture was allowed to stand under ice cooling for 30 minutes and then at room temperature for one hour, the solvent was removed under reduced pressure. The residue was subjected to purification using 3.0 ml of silica gel (Wako Gel C-200). The by-product, BzlO-PEG-Ala-Val-DNR, was removed by elution using, as the developer, 10 ml each of chloroform-methanol mixtures (10:1, 7:1, 5:1, 3:1, 2:1). Then, the desired HO-PEG-Ala-Val-DNR was eluted with 20 ml of a mixture of chloroform:methanol:water (13:6:1). The solvent was removed from the desired fraction under reduced pressure to give 38 μg (0.03 μmol) of HO-PEG-Ala-Val-DNR (yield from daunorubicin: 1.8%).

Silica gel thin layer chromatography: Kieselgel 60 (Merck & Co., Inc.); Chloroform:methanol:water=13:6:1; Rf value: 0.6; $^1$HNMR spectrum (500 MHz, in CDCl$_3$) δ (ppm): PEG-Ala-Val moiety 4.19 (4H, s, OCH$_2$), 3.49 (4nH, brs, OCH$_2$CH$_2$), 3.20 [1H, brs, CH(Ala)], 2.29 [1H, brq, J=5.7 Hz, CH(Val)], 1.29 [1H, s, CH(Val)], 1.24 [3H, d, J=2.8 Hz, CH$_3$(Ala)], 0.95 [6H, brm, CH$_3$(Val)], Daunorubicin moiety 7.82 (2H, m, H-1, H-2), 7.72 (1H, m, H-3), 5.34 (1H, d, J=3.7 Hz, H-1'), 5.27 (1H, brs, H-7), 4.31 (1H, q, J=6.5 Hz, H-5'), 4.19 (3H, s, 4-OCH$_3$), 3.29 (1H, d, J=18 Hz, H-10b), 3.12 (1H, d, J=18 Hz, H-10a), 2.80 (3H, s, H-14), 2.34 (1H, brd, J=14 Hz, H-8b), 2.22 (1H, d, J=14 Hz, H-8a), 1.91 (1H, brm, H-2'b), 1.83 (1H, brm, H-2'a), 1.29 (3H, d, J=6.5 Hz, 5'-CH$_3$); Ultraviolet absorption spectrum (in methanol, λ$_{max}$): 232, 274, 495, 534, 575 nm; Infrared absorption spectrum (in chloroform): 3580, 3400, 3000, 2924, 2870, 1786, 1717, 1660, 1605, 1520, 1450, 1295, 1105 cm$^{-1}$ REFERENCE EXAMPLE 10
Compound (XI-5): HO-PEG-Ala-Pro-DNR In 0.5 ml of methylene chloride was dissolved 9.7 mg (11.3 μmol) of Compound (VIII-2) obtained in Reference Example 2, and 3.1 mg (26.9 μmol) of HONSu and 5.5 mg (26.7 μmol) of DCC were added thereto under ice cooling, followed by stirring at 0° C. for 2 hours. The insoluble matter (DCU) was removed by filtration, and the solvent was removed from the filtrate under reduced pressure. Then the residue was dissolved in 300 μl of methanol in a stream of nitrogen, and 2–3 mg of 10% palladium carbon catalyst was added thereto, followed by vigorous stirring in a stream of hydrogen at room temperature for 2 hours. After removal of the catalyst by filtration, the solvent was removed from the filtrate under reduced pressure. To the residue was added under ice cooling 165 μl (0.5 μmol) of a solution prepared by dissolving 0.9 mg of daunorubicin hydrochloride in 500 μl of a solution of triethylamine in dry DMF (0.48 μg/ml). After the resulting mixture was allowed to stand under ice cooling for 30 minutes and then at room temperature for one hour, the solvent was removed under reduced pressure. The residue was subjected to purification using 5.0 ml of silica gel (Wako Gel C-200). The by-product, BzlO-PEG-Ala-Pro-DNR, was removed by elution using, as the developer, 10 ml each of chloroform-methanol mixtures (10:1, 7:1, 5:1, 3:1, 2:1). Then, the desired HO-PEG-Ala-Pro-DNR was eluted with 20 ml of a mixture of chloroform:methanol:water (13:6:1). The solvent was removed from the desired fraction under reduced pressure to give 150 μg (0.1 μmol) of HO-PEG-Ala-Pro-DNR (yield from daunorubicin: 20%).

Silica gel thin layer chromatography: Kieselgel 60 (Merck & Co., Inc.); Chloroform:methanol:water=13:6:1; Rf value: 0.6; $^1$HNMR spectrum (500 MHz, in CDCl$_3$) δ (ppm): PEG-Ala-Pro moiety 4.52 [2H, br, CH$_2$(Pro)], 4.12 (4H, s, OCH$_2$), 3.75 [1H, q, J=6.0 Hz, CH(Ala)], 3.64 (4nH, brs, OCH$_2$CH$_2$), 3.42 [2H, br, CH$_2$(Pro)], 2.37 [1H, br, CH(Pro)], 2.08 [2H, brm, CH$_2$(Pro)], 1.29 [3H, br, CH$_3$(Ala)], Daunorubicin moiety 8.03 (2H, m, H-1, H-2), 7.72 (1H, m, H-3), 5.52 (1H, brd, J=3.7 Hz, H-1'), 5.36 (1H, brm, H-1'), 5.29 (1H, brs, H-7), 4.34 (1H, q, J=6.5 Hz, H-5'), 4.09 (3H, s, 4-OCH$_3$), 3.23 (1H, d, J=18 Hz, H-10b), 3.01 (1H, d, J=18 Hz, H-10a), 2.80 (3H, s, H-14), 2.42 (1H, brd, J=14 Hz, H-8b), 2.23 (1H, d, J=14 Hz, H-8a), 2.06 (1H, brm, H-2'b), 1.87 (1H, brm, H-2'a), 1.29 (3H, d, J=6.5 Hz, 5'-CH$_3$); Ultraviolet absorption spectrum (in methanol, λ$_{max}$): 232, 251, 290, 469, 495, 532, 580 nm; Infrared absorption spectrum (in chloroform): 3690, 3580, 3400, 3015, 2936, 2878, 1782, 1714, 1650, 1600, 1525, 1457, 1432, 1350, 1285, 1240, 1108 cm$^{-1}$

REFERENCE EXAMPLE 11
Compound (XI-6): HO-PEG-Gly-Pro-DNR

In 0.5 ml of methylene chloride was dissolved 11.0 mg (12.8 μmol) of Compound (VIII-3) obtained in Reference Example 3, and 3.5 mg (30.4 μmol) of HONSu and 6.3 mg (30.5 μmol) of DCC were added thereto under ice cooling, followed by stirring at 0° C. for 2 hours. The insoluble matter (DCU) was removed by filtration, and the solvent was removed from the filtrate under reduced pressure. Then the residue was dissolved in 300 μl of methanol in a stream of nitrogen, and 2–3 mg of 10% palladium carbon catalyst was added thereto, followed by vigorous stirring in a stream of hydrogen at room temperature for 2 hours. After removal of the catalyst by filtration, the solvent was removed from the filtrate under reduced pressure. To the residue was added under ice cooling 156 μl (0.5 μmol) of a solution prepared by dissolving 0.9 mg of daunorubicin hydrochloride in 500 μl of a solution of triethylamine in dry DMF (0.48 μg/ml). After the resulting mixture was allowed to stand under ice cooling for 30 minutes and then at room temperature for one hour, the solvent was removed under reduced pressure. The residue was subjected to purification using 5.0 ml of silica gel (Wako Gel C-200). The by-product, BzlO-PEG-Gly-Pro-DNR, was removed by elution using, as the developer, 10 ml each of chloroform-methanol mixtures (10:1, 7:1, 5:1, 3:1, 2:1). Then, the desired HO-PEG-Gly-Pro-DNR was eluted with 20 ml of a mixture of chloroform:methanol:water (13:6:1). The solvent was removed from the desired fraction under reduced pressure to give 180 μg (0.1 μmol) of HO-PEG-Gly-Pro-DNR (yield from daunorubicin: 26%).

Silica gel thin layer chromatography: Kieselgel 60 (Merck & Co., Inc.); Chloroform:methanol:water=13:6:1; Rf value: 0.6; $^1$HNMR spectrum (500 MHz, in CDCl$_3$) δ (ppm): PEG-Gly-Pro moiety 4.51 [2H, brm, CH$_2$(Pro)], 4.17 (4H, m, OCH$_2$O), 3.64 (4nH, brs, OCH$_2$CH$_2$), 3.56 [2H, s, CH$_2$(Gly)], 3.50 [2H, m, CH$_2$(Pro)], 2.21 [1H, s, CH(Pro)], 2.02 [2H, brm, CH$_2$(Pro)], Daunorubicin moiety 8.04 (2H, m, H-1, H-2), 7.79 (1H, m, H-3), 5.34 (1H, d, J=3.7 Hz, H-1'), 5.27 (1H, brs, H-7), 4.52 (1H, q, J=6.7 Hz, H-5'), 4.12 (3H, s, 4-OCH$_3$), 3.22 (1H, d, J=18 Hz, H-10b), 2.99 (1H, d, J=18 Hz, H-10a), 2.90 (3H, s, H-14), 2.35 (1H, brd, J=14 Hz, H-8b), 2.22 (1H, d, J=14 Hz, H-8a), 2.02 (1H, brm, H-2'b), 1.18 (3H, d, J=6.6 Hz, 5'-CH$_3$); Ultraviolet absorption spectrum (in methanol, λ$_{max}$): 235, 252, 289, 470, 495, 534, 578 nm; Infrared absorption spectrum (in chloroform): 3580, 3000, 2930, 2880, 1790, 1719, 1658, 1610, 1450, 1404, 1350, 1290, 1110 cm$^{-1}$

REFERENCE EXAMPLE 12
Compound (XI-7): HO-PEG-Ala-Val-Compound (20)

In 0.5 ml of methylene chloride was dissolved 11.5 mg (13.4 μmol) of Compound (VIII-1) obtained in Reference Example 1, and 3.6 mg (31.3 μmol) of HONSu and 6.4 mg (31.0 μmol) of DCC were added thereto under ice cooling, followed by stirring at 0° C. for 2 hours. The insoluble matter (DCU) was removed by filtration, and the solvent was removed from the filtrate under reduced pressure. Then the residue was dissolved in 300 μl of methanol in a stream of nitrogen, and 2–3 mg of 10% palladium carbon catalyst was added thereto, followed by vigorous stirring in a stream of hydrogen at room temperature for 2.5 hours. After removal of the catalyst by filtration, the solvent was removed from the filtrate under reduced pressure. The residue was dissolved in a small amount of chloroform and subjected to purification using 3.0 ml of silica gel (Wako Gel C-200). The benzyl ester form, BzlO-PEG-Ala-Val-ONSu, was removed by elution using, as the developer, 10 ml each of chloroform-methanol mixtures (20:1, 10:1). Then, a solution prepared by dissolving 0.05 mg (0.10 μmol) of Compound (20) obtained in Reference Example 17 in 200 μl of dry DMF was charged into the column. After 150 μl of dry DMF was further applied to the column, the mixture was subjected to reaction at room temperature for 30 minutes. After washing of the column using 10 ml each of chloroform-methanol mixtures (10:1, 5:1, 2:1) as the developer, the desired HO-PEG-Ala-Val-Compound (20) was eluted with 10 ml of a mixture of chloroform:methanol:water (13:6:1). The solvent was removed from the desired fraction under reduced pressure to give 112 μg (0.09 μmol) of HO-PEG-Ala-Val-Compound (20) [yield from Compound (20): 88%].

Silica gel thin layer chromatography: Kieselgel 60 (Merck & Co., Inc.); Chloroform:methanol:water=13:6:1; Rf value: 0.6; $^1$HNMR spectrum (500 MHz, in CDCl$_3$) δ (ppm): PEG-Ala-Val moiety 4.12 (4H, s, OCH$_2$), 3.64 (4nH, brs, OCH$_2$CH$_2$), 3.23 [1H, s, CH(Ala)], 2.23 (1H, brq, J=6.0 Hz, CH(Val)], 1.26 [1H, s, CH(Val)], 1.17 [3H, d, J=2.8 Hz, CH$_3$(Ala)], 0.89 [6H, q, J=2.5 Hz, CH$_3$(Val)], Compound (20) moiety 10.57 (1H, brs), 7.68 (1H, d, J=15.5 Hz), 7.12 (1H, dd, J=8.3, 2.0 Hz), 6.99 (1H, d, J=2.0 Hz), 6.80 (1H, d, J=8.1 Hz), 4.40 (1H, m), 4.27 (2H, m), 4.16 (1H, brd, J=11.2 Hz), 3.90 (3H, s), 3.82 (3H, s), 3.67 (1H, m), 3.12 (2H, t, J=7.1 Hz), 2.63 (3H, s), 2.38 (1H, dd, J=7.5, 3.4 Hz), 1.52 (2H, m), 1.37 (1H, t, J=4.2 Hz); Infrared absorption spectrum (in chloroform): 3690, 3592, 3400, 3000, 2900, 1712, 1650, 1600, 1450, 1300, 1110 cm$^{-1}$

REFERENCE EXAMPLE 13
Compound (XI-8): HO-PEG-Ala-Pro-Compound (20)

In 0.5 ml of methylene chloride was dissolved 9.8 mg (11.4 μmol) of Compound (VIII-2) obtained in Reference Example 2, and 3.2 mg (27.8 μmol) of HONSu and 5.6 mg (27.1 μmol) of DCC were added thereto under ice cooling, followed by stirring at 0° C. for 2 hours. The insoluble matter (DCU) was removed by filtration, and the solvent was removed from the filtrate under reduced pressure. Then the residue was dissolved in 300 μl of methanol in a stream of nitrogen, and 2–3 mg of 10% palladium carbon catalyst was added thereto, followed by vigorous stirring in a stream of hydrogen at room temperature for 3 hours. After removal of the catalyst by filtration, the solvent was removed from the filtrate under reduced pressure. The residue was dissolved in a small amount of chloroform and subjected to purification using 3.0 ml of silica gel (Wako Gel C-200). The benzyl ester form, BzlO-PEG-Ala-Pro-ONSu, was removed by elution using, as the developer, 10 ml each of chloroform-methanol mixtures (20:1, 10:1). Then, a solution prepared by dissolving 0.05 mg (0.10 μmol) of Compound (20) obtained in Reference Example 17 in 200 μl of dry DMF was charged into the column. After 100 μl of dry DMF was further applied to the column, the mixture was subjected to reaction at room temperature for 30 minutes. After washing of the column using 10 ml each of chloroform-methanol mixtures (10:1, 2:1) as the developer, the desired HO-PEG-Ala-Pro-Compound (20) was eluted with 10 ml of a mixture of chloroform:methanol:water (13:6:1). The solvent was removed from the desired fraction under reduced pressure to give 233 μg (0.10 μmol) of HO-PEG-Ala-Pro-Compound (20) [yield from Compound (20): 100%].

Silica gel thin layer chromatography: Kieselgel 60 (Merck & Co., Inc.); Chloroform:methanol:water=13:6:1; Rf value: 0.6; $^1$HNMR spectrum (500 MHz, in CDCl$_3$) δ (ppm): PEG-Ala-Pro moiety 4.52 [2H, brm, CH$_2$(Pro)], 4.12 (4H, s, OCH$_2$), 3.64 (4nH, brs, OCH$_2$CH$_2$), 3.42 (2H, br, CH$_2$(Pro)], 3.23 [1H, s, CH(Ala)], 2.37 [1H, br, CH(Pro)], 2.08 [2H, brm, CH$_2$(Pro)], 1.17 [3H, d, J=2.8 Hz, CH$_3$(Ala)], Compound (20) moiety 10.23 (1H, brs), 7.68 (1H, d, J=15.5

Hz), 7.10 (1H, dd, J=8.3, 2.0 Hz), 6.89 (1H, d, J=2.0 Hz), 6.80 (1H, d, J=8.1 Hz), 4.40 (1H, m), 4.29 (2H, m), 4.20 (1H, brd, J=11.2 Hz), 3.89 (3H, s), 3.82 (3H, s), 3.67 (1H, m), 3.12 (2H, t, J=7.1 Hz), 2.63 (3H, s), 2.33 (1H, dd, J=7.5, 3.4 Hz), 1.52 (2H, m), 1.35 (1H, t, J=4.2 Hz); Infrared absorption spectrum (in chloroform): 3690, 3592, 3400, 3000, 2900, 1712, 1650, 1600, 1450, 1300, 1110 cm$^{-1}$

REFERENCE EXAMPLE 14

Compound (XI-9): HO-PEG-Gly-Pro-Compound (20)

In 0.5 ml of methylene chloride was dissolved 11.2 mg (13.0 μml) of Compound (VIII-3) obtained in Reference Example 3, and 3.6 mg (31.3 μmol) of HONSu and 6.4 mg (31.0 μmol) of DCC were added thereto under ice cooling, followed by stirring at 0° C. for 2 hours. The insoluble matter (DCU) was removed by filtration, and the solvent was removed from the filtrate under reduced pressure. Then the residue was dissolved in 300 μl of methanol in a stream of nitrogen, and 2–3 mg of 10% palladium carbon catalyst was added thereto, followed by vigorous stirring in a stream of hydrogen at room temperature for 3 hours. After removal of the catalyst by filtration, the solvent was removed from the filtrate under reduced pressure. The residue was dissolved in a small amount of chloroform and subjected to purification using 3.0 ml of silica gel (Wako Gel C-200). The benzyl ester form, BzlO-PEG-Gly-Pro-ONSu, was removed by elution using, as the developer, 10 ml each of chloroform-methanol mixtures (20:1, 10:1). Then, a solution prepared by dissolving 0.05 mg (0.10 μmol) of Compound (20) obtained in Reference Example 17 in 200 μl of dry DMF was charged into the column. After 150 μl of dry DMF was further applied to the column, the mixture was subjected to reaction at room temperature for 30 minutes. After washing of the column using 10 ml each of chloroform-methanol mixtures (10:1, 2:1) as the developer, the desired HO-PEG-Gly-Pro-Compound (20) was eluted with 10 ml of a mixture of chloroform:methanol:water (13:6:1). The solvent was removed from the desired fraction under reduced pressure to give 135 μg (0.10 μmol) of HO-PEG-Gly-Pro-Compound (20) [yield from Compound (20): 100%].

Silica gel thin layer chromatography: Kieselgel 60 (Merck & Co., Inc.); Chloroform:methanol:water=13:6:1; Rf value: 0.6; $^{1}$HNMR spectrum (500 MHz, in CDCl$_3$) δ (ppm): PEG-Gly-Pro moiety 4.22 [2H, brm, CH$_2$(Pro)], 4.17 (4H, m, OCH$_2$), 4.08 [2H, s, CH$_2$(Gly)], 3.64 (4nH, brs, OCH$_2$CH$_2$), 3.52 [2H, br, CH$_2$(Pro)], 2.22 [1H, br, CH(Pro)], 1.95 [2H, brm, CH$_2$(Pro)], Compound (20) moiety 9.97 (1H, brs), 7.54 (1H, d, J=15.5 Hz), 7.22 (1H, dd, J=8.3, 2.0 Hz), 6.99 (1H, d, J=2.0 Hz), 6.88 (1H, d, J=8.1 Hz), 4.40 (1H, m), 4.27 (2H, m), 4.16 (1H, brd, J=11.2 Hz), 3.90 (3H, s), 3.82 (3H, s), 3.70 (1H, m), 3.12 (2H, t, J=7.1 Hz), 2.63 (3H, s), 2.54 (1H, dd, J=7.5, 3.4 Hz), 1.62 (2H, m), 1.35 (1H, t, J=4.2 Hz); Infrared absorption spectrum (in chloroform): 3690, 3592, 3400, 3000, 2900, 1712, 1650, 1600, 1450, 1300, 1110 cm$^{-1}$

REFERENCE EXAMPLE 15

Compound (12)

Compound (12) was synthesized according to the following reaction steps.

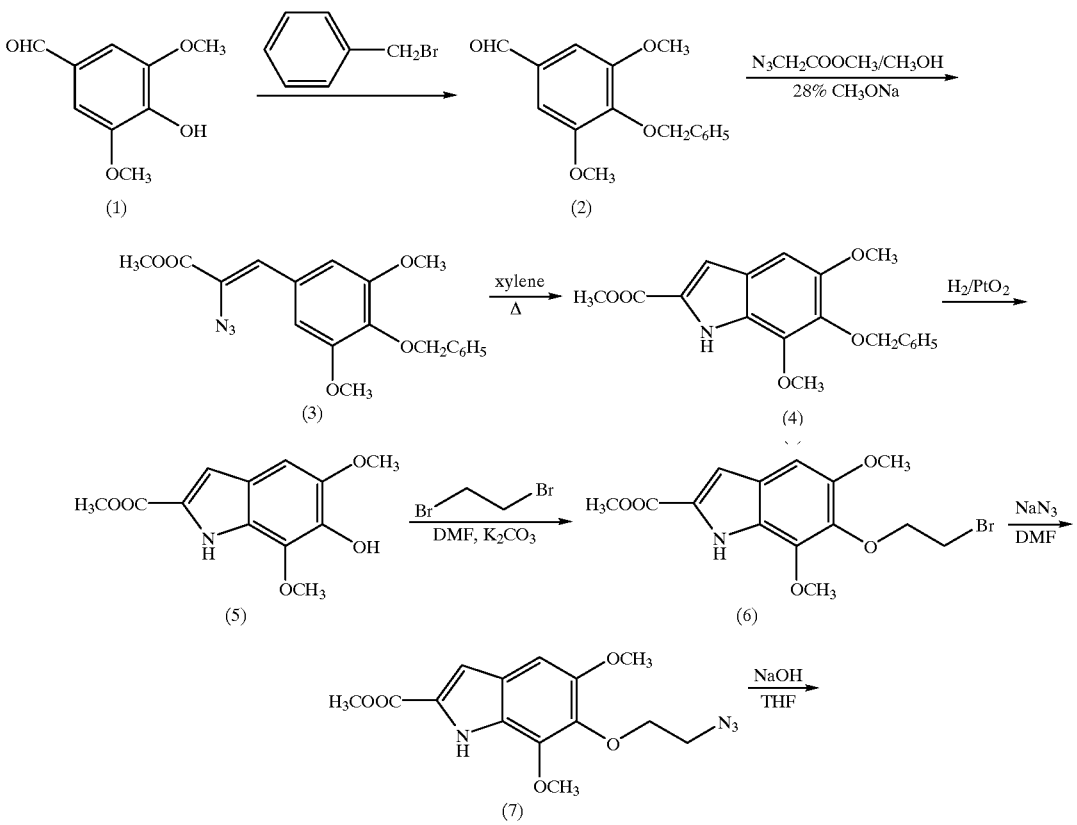

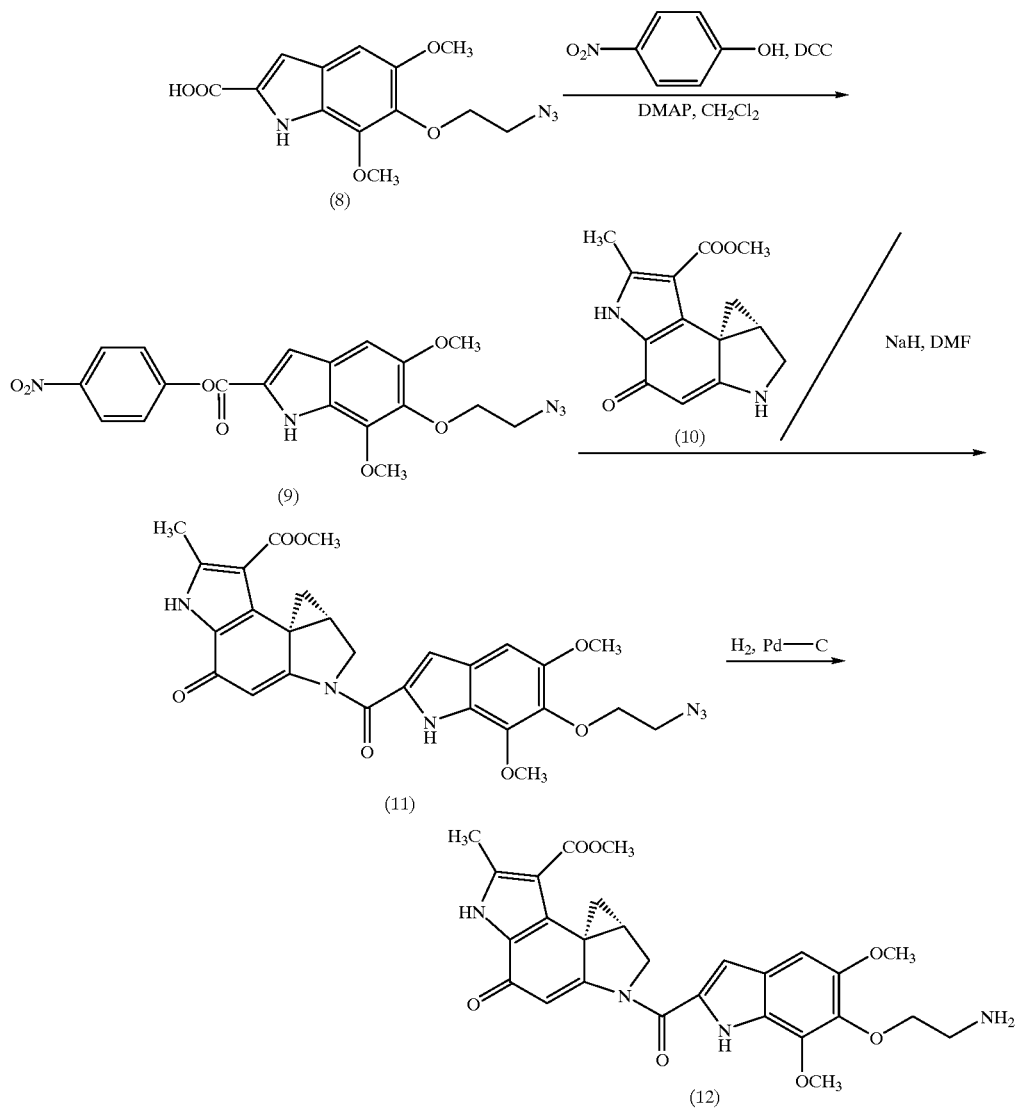

In 30 ml of DMF was dissolved 3.0 g (16 mmol) of 4-hydroxy-3,5-dimethoxybenzaldehyde [Compound (1)], and 3.4 g of anhydrous potassium carbonate was added thereto. To the resulting solution was added dropwise 3.0 ml (25 mmol) of benzyl bromide, followed by stirring at room temperature for 24 hours. After addition of 300 ml of 0.1 N HCl, the resulting mixture was extracted twice with 200 ml portions of ethyl acetate. The ethyl acetate layer was washed with a saturated aqueous solution of sodium chloride, and then dried over anhydrous sodium sulfate. After the solvent was removed under reduced pressure, the residue was subjected to purification using 300 ml of silica gel (Wako Gel C-200), and as the developer, a hexane:ethyl acetate mixture (3:1). The solvent was removed from the desired fractions under reduced pressure to give 4.7 g (17 mmol) of Compound (2) (yield: 100%).

In 70 ml of methanol was dissolved 11.8 g (103 mmol) of methyl azidoacetate in a stream of argon, and 20.9 ml (103 mmol) of 28% sodium methoxide was added dropwise thereto at −50° C. over 75 minutes, followed by stirring for 30 minutes. To the resulting solution was added 40 ml of a solution of 4.7 g of Compound (2) in a methanol-toluene mixture (1:1) over 25 minutes, and the temperature of the mixture was allowed to rise from −50° C. to about −10° C. with stirring for 24 hours. Then, appropriate amounts of water and diethyl ether were added thereto to extract the ether layer. The ether layer was washed with a saturated aqueous solution of sodium chloride and dried over anhydrous sodium sulfate, and the solvent was removed under reduced pressure to give 2.8 g (7.6 mmol) of Compound (3) (yield: 45%).

In 750 ml of xylene was dissolved 2.8 g of Compound (3), and the solution was heated at 140 to 150° C. for 2 hours. After the solution was cooled to room temperature, the solvent was removed under reduced pressure. The residue was subjected to purification using 150 ml of silica gel (Wako Gel C-200), and as the developer, a hexane-ethyl acetate mixture (4:1). The solvent was removed from the desired fractions under reduced pressure to give 2.4 g (7.0 mmol) of Compound (4) (yield: 93%).

In 116 ml of a tetrahydrofuran-methanol mixture (1:1) was dissolved 2.4 g of Compound (4), and 471 mg of platinum dioxide was added thereto, followed by vigorous stirring in a stream of hydrogen for 24 hours. To the resulting mixture was added 200 mg of platinum dioxide, followed by further stirring in a stream of hydrogen for 7 hours. The catalyst was removed by filtration using Celite, and the solvent was removed from the filtrate under reduced pressure. The residue was subjected to purification using a column of silica gel (120 ml), and as the developer, a hexane-ethyl acetate mixture (3:1). The solvent was removed from the desired fractions under reduced pressure to give 1.6 g (6.4 mmol) of Compound (5) (yield: 91%).

In 5 ml of DMF was dissolved 100 mg (0.4 mmol) of Compound (5), and 275 mg (2 mmol) of anhydrous potassium carbonate was added thereto. To the resulting solution was added dropwise 173 µl (2 mmol) of 1,2-dibromoethane, followed by stirring in a stream of nitrogen at room temperature for 19 hours. After addition of a phosphate buffer (pH 7), the mixture was extracted with ethyl acetate. The ethyl acetate layer was washed with a saturated aqueous solution of sodium chloride, and then dried over anhydrous sodium sulfate. After the solvent was removed under reduced pressure, the residue was subjected to purification using 20 ml of silica gel (Wako Gel C-200), and as the developer, a hexane-ethyl acetate mixture (2:1). The solvent was removed from the desired fractions under reduced pressure to give 94 mg (0.26 mmol) of Compound (6) (yield: 65%).

In 9.5 ml of DMF was dissolved 94 mg (0.26 mmol) of Compound (6), and 85 mg (1.3 mmol) of sodium azide was added thereto, followed by stirring at room temperature for 25 hours. To the resulting solution were added appropriate amounts of ethyl acetate and a phosphate buffer (pH 7) to extract the ethyl acetate layer. After the ethyl acetate layer was dried over anhydrous sodium sulfate, the solvent was removed under reduced pressure to give 79 mg of Compound (7) (yield: 95%).

In a mixture of THF (8 ml) and water (10 ml) was dissolved 79 mg of Compound (7), and 2.5 ml of 1N aqueous solution of sodium hydroxide was added thereto, followed by stirring at room temperature for 3.5 hours. The reaction mixture was made acidic by addition of 1N HCl, and extracted using chloroform. The chloroform layer was washed with a saturated aqueous solution of sodium chloride and dried over anhydrous sodium sulfate, and the solvent was removed under reduced pressure to give 75 mg of Compound (8) (yield: 98%).

In 7 ml of methylene chloride was dissolved 75 mg of Compound (8) under ice cooling, and 103 mg (0.5 mmol) of DCC was added thereto, followed by stirring under ice cooling for one hour. To the resulting solution were added 70 mg (0.5 mmol) of p-nitrophenol and 61 mg (0.5 mmol) of dimethylaminopyridine, followed by stirring at a temperature of 0° C. to room temperature for 80 minutes. The insoluble matter was removed by filtration, and 0.5 N HCl was added to the filtrate, followed by extraction with chloroform. The chloroform layer was washed with a saturated aqueous solution of sodium hydrogencarbonate and a saturated aqueous solution of sodium chloride, and then dried over anhydrous sodium sulfate. After the solvent was removed under reduced pressure, the product was recrystallized from ethanol to give 72 mg of Compound (9) (yield: 69%).

In a stream of argon, 37 mg (0.9 mmol) of 50% sodium hydride was dissolved in 1.5 ml of DMF, and a solution prepared by dissolving 185 mg (0.7 mmol) of Compound (10) obtained according to the method described in Japanese Published Unexamined Patent Application No. 178858/93 in 2.9 ml of DMF was added thereto at −20° C., followed by stirring for 3 hours. To the resulting solution was added a solution prepared by dissolving 368 mg (0.9 mmol) of Compound (9) in 6 ml of DMF, and the temperature of the mixture was allowed to rise from −20° C. to room temperature with stirring for 24 hours. To the resulting mixture were added appropriate amounts of ethyl acetate and a phosphate buffer (pH 7.0) to extract the ethyl acetate layer. The ethyl acetate layer was washed with a saturated aqueous solution of sodium chloride, and dried over anhydrous sodium sulfate. After the solvent was removed under reduced pressure, the residue was subjected to purification using 80 ml of silica gel, and as the developer, a chloroform-methanol mixture (100:1). The solvent was removed from the desired fractions under reduced pressure to give 278 mg (0.5 mmol) of Compound (11) (yield: 71%).

The structures of Compounds (2) to (9) and Compound (11) were confirmed by $^1$H-NMR and mass spectrometric analysis.

In a stream of nitrogen, 20 mg (36.6 µmol) of Compound (11) was dissolved in 1.1 ml of a mixture of acetic acid (0.2 ml) and tetrahydrofuran (9.8 ml), and 7.3 mg of 10% palladium carbon catalyst was added thereto at 10° C. to 15° C., followed by vigorous stirring in a stream of hydrogen at 10° C. to 15° C. for 3 hours and 20 minutes. After the mixture was cooled to a temperature below −20° C. and the catalyst was removed by filtration, the solvent was removed under reduced pressure under cooling to give 9 mg (17.3 µmol) of Compound (12) (yield: 47%).

$^1$HNMR spectrum (500 MHz, in CDCl$_3$) δ (ppm): 11.58 (1H, brs, 1-NH), 9.40 (1H, brs, 1'-NH), 7.12 (1H, s, H-7), 6.95 (1H, d, J=2.3 Hz, H-3'), 6.81 (1H, s, H-4'), 4.45 (2H, m, H-5), 4.08 (3H, s, 7'-OCH$_3$), 3.92 (2H, t, J=5.2 Hz, OCH$_2$), 3.90 (3H, s, 5'-OCH$_3$), 3.82 (3H, s, 3-COOCH$_3$), 3.67 (1H, m, H-4a), 3.20 (2H, q, J=6.4 Hz, CH$_2$), 2.63 (3H, s, 2-CH$_3$), 2.38 (1H, dd, J=7.5, 3.4 Hz, H-4), 1.37 (1H, t, J=4.2 Hz, H-4); Mass spectrum (SIMS): 521 (M+H)

REFERENCE EXAMPLE 16

Compound (X-1): BzlO-PEG-Ala-Val-Compound (12)

In 2.4 ml of methylene chloride was dissolved 13 mg (15.2 µmol) of Compound (VIII-1) obtained in Reference Example 1, and 2.0 mg of HONSu and 4.3 mg of DCC were successively added thereto under ice cooling, followed by stirring for 2 hours. The insoluble matter was removed by filtration, and the solvent was removed from the filtrate under reduced pressure. Then the residue was dissolved in 2 ml of pyridine, followed by addition of a solution prepared by dissolving 7.8 mg (15.0 µmol) of Compound (12) obtained in Example 24 in 1.5 ml of pyridine under ice cooling. The resulting mixture was stirred under ice cooling for one hour, and then at room temperature for 2 hours. After the solvent was removed under reduced pressure, the residue was subjected to purification using 5 ml of silica gel (Wako Gel C-200), and as the developer, 5 ml each of chloroform-methanol mixtures (100:1, 80:1, 60:1, 40:1, 20:1, 10:1, 5:1). The eluate was taken in 0.5 ml fractions. The solvent was removed from the desired fractions under reduced pressure to give 2.8 mg (0.2 µmol) of BzlO-PEG-Ala-Val-Compound (12) (yield: 1.4%).

Silica gel thin layer chromatography: Kieselgel 60 (Merck & Co., Inc.); Chloroform:methanol=10:1; Rf value: 0.5;

¹HNMR spectrum (500 MHz, in CDCl₃) δ (ppm): BzlO-PEG-Ala-Val moiety 7.36 (5H, m, C₆H₅), 5.19 (2H, s, CH₂), 4.12 (4H, s, OCH₂), 3.64 (4nH, brs, OCH₂CH₂), 3.23 [1H, s, CH(Ala)], 2.23 [1H, brq, J=6.0 Hz, CH(Val)], 1.26 [1H, s, CH(Val)], 1.17 [3H, d, J=2.8 Hz, CH₃(Ala)], 0.89 [6H, q, J=2.5 Hz, CH₃(Val)], Compound (12) moiety 11.58 (1H, brs, 1-NH), 9.40 (1H, brs, 1'-NH), 7.12 (1H, s, H-7), 6.95 (1H, d, J=2.3 Hz, H-3'), 6.81 (1H, s, H-4'), 4.45 (2H, m, H-5), 4.08 (3H, s, 7'-OCH₃), 3.90 (3H, s, 5'-OCH₃), 3.88 (2H, t, J=5.2 Hz, OCH₃), 3.82 (3H, s, 3-COOCH₃), 3.67 (1H, m, H-4a), 3.20 (2H, q, J=6.4 Hz, CH₂), 2.63 (3H, s, 2-CH₃), 2.38 (1H, dd, J=7.5, 3.4 Hz, H-4), 1.37 (1H, t, J=4.2 Hz, H-4); Infrared absorption spectrum (in chloroform): 3595, 3450, 3010, 2900, 1750, 1665, 1608, 1515, 1460, 1310, 1110 cm⁻¹

REFERENCE EXAMPLE 17

Compound (20)

Compound (20) was synthesized according to the following reaction steps.

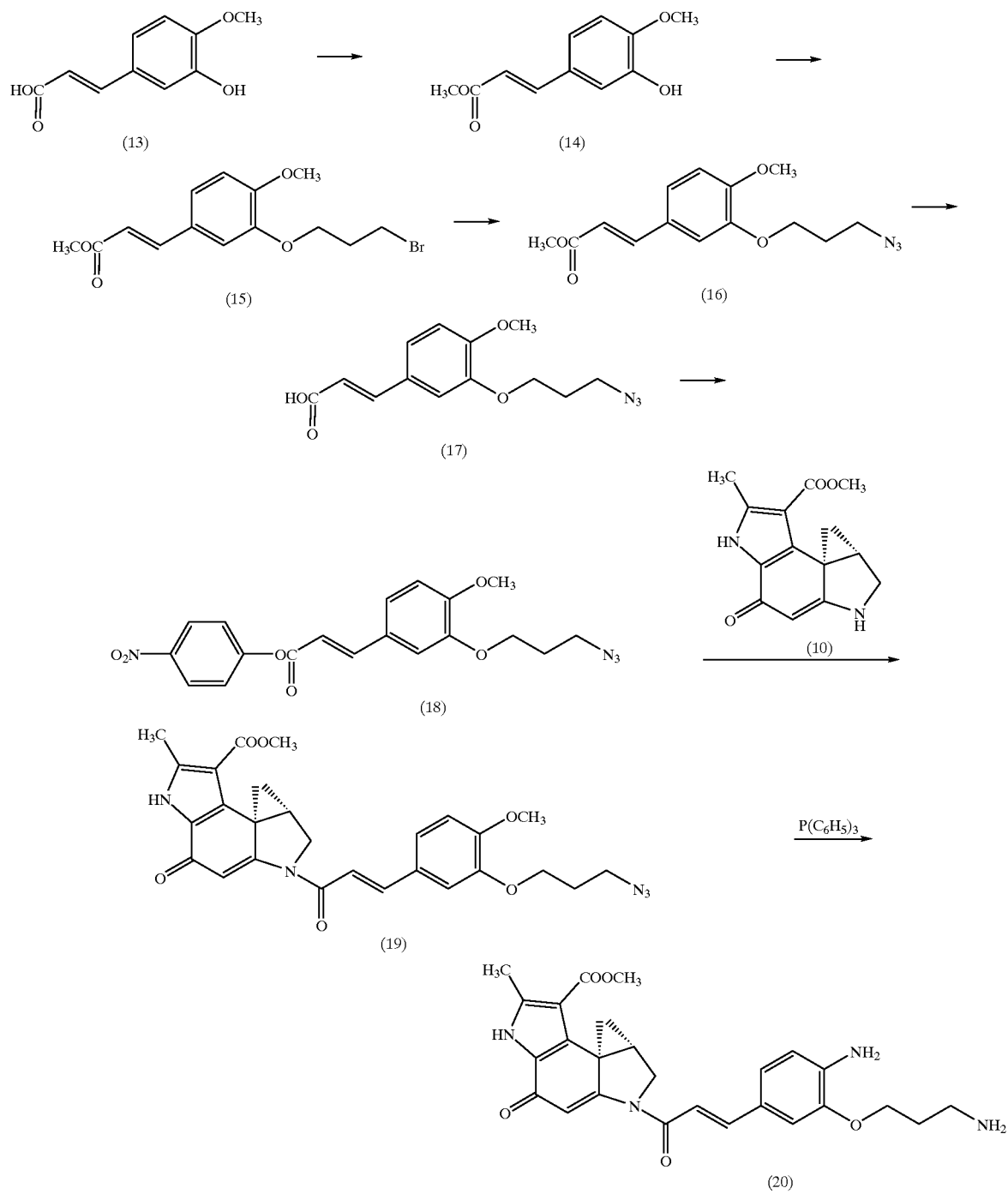

In a mixture of methanol (30 ml) and benzene (105 ml) was dissolved 1.51 g (7.78 mmol) of 3'-hydroxy-4'-methoxycinnamic acid [Compound (13)], and 11 ml (9.6 mmol) of a 10% solution of trimethylsilyl diazomethane in hexane was added thereto, followed by stirring at room temperature for 3 hours. To the resulting solution was added 2.0 ml of a 10% solution of trimethylsilyl diazomethane in hexane, followed by stirring for one hour. After addition of a saturated aqueous solution of sodium hydrogencarbonate, the reaction mixture was extracted with ethyl acetate. The ethyl acetate layer was washed with a saturated aqueous solution of sodium chloride and dried over anhydrous sodium sulfate, and the solvent was removed under reduced pressure to give 1.55 g of methyl ester of 3'-hydroxy-4'-methoxycinnamic acid [Compound (14)] (yield: 95.6%).

In 60 ml of DMF was dissolved 1.55 g (7.44 mmol) of Compound (14), and 5.14 g (37.2 mmol) of potassium carbonate and 3.78 ml (37.2 mmol) of 1,3-dibromopropane were added thereto, followed by stirring at room temperature for 14 hours. To the resulting solution were added water and ethyl acetate to extract the ethyl acetate layer. The ethyl acetate layer was washed with water and a saturated aqueous solution of sodium chloride, and then dried over anhydrous sodium sulfate. After the solvent was removed under reduced pressure, the residue was subjected to purification by silica gel chromatography using a hexane-ethyl acetate mixture (4:1) as the developer to give 1.90 g of methyl ester of 3'-(3-bromopropyloxy)-4'-methoxycinnamic acid [Compound (15)] (yield: 77.6%).

In 120 ml of DMF was dissolved 1.90 g (5.77 mmol) of Compound (15), and 1.88 g (28.9 mmol) of sodium azide was added thereto, followed by stirring at room temperature for 17 hours. To the resulting solution was added a saturated aqueous solution of sodium hydrogencarbonate, followed by extraction with ethyl acetate. The ethyl acetate layer was washed with water and a saturated aqueous solution of sodium chloride, and then dried over anhydrous sodium sulfate. The solvent was removed under reduced pressure to give 1.81 g of crude methyl ester of 3'-(3-azidopropyloxy)-4'-methoxycinnamic acid [Compound (16)].

$^1$HNMR spectrum (100 MHz, in $CDCl_3$) δ (ppm): 7.62 (1H, d, J=15.8 Hz), 7.12 (1H, d, J=7.9 Hz), 7.08 (1H, s), 6.86 (1H, d, J=7.9 Hz), 6.29 (1H, d, J=15.8 Hz), 4.12 (2H, t, J=6.2 Hz), 3.89 (3H, s), 3.79 (3H, s), 3.55 (2H, t, J=6.6 Hz), 2.10 (2H, m)

In a mixture of THF (60 ml) and water (2 ml) was dissolved 1.81 g of crude Compound (16), and 11.5 ml of 1N aqueous solution of sodium hydroxide was added thereto, followed by stirring at room temperature for 19 hours. After the reaction mixture was adjusted to pH 4 by addition of 2N HCl, water and ethyl acetate were added thereto to extract the ethyl acetate layer. The ethyl acetate layer was washed with water and a saturated aqueous solution of sodium chloride, and then dried over anhydrous sodium sulfate. The solvent was removed under reduced pressure to give 1.64 g of crude 3'-(3-azidopropyloxy)-4'-methoxycinnamic acid [Compound (17)].

In 150 ml of methylene chloride was dissolved 5.77 mmol of Compound (17), and 1.36 g (9.8 mmol) of 4-nitrophenol, 2.73 ml (19.6 mmol) of triethylamine and 2.51 g (9.8 mmol) of 2-chloro-1-methylpyridinium iodide were added thereto, followed by stirring at room temperature for 5 hours. To the resulting solution were further added 722 mg (5.2 mmol) of 4-nitrophenol, 1.45 ml (10.4 mmol) of triethylamine and 1.33 g (5.2 mmol) of 2-chloro-1-methylpyridinium iodide, followed by stirring for 17 hours. After addition of a saturated aqueous solution of sodium hydrogencarbonate, the reaction mixture was extracted with chloroform. The chloroform layer was washed with a saturated aqueous solution of sodium hydrogencarbonate and dried over anhydrous sodium sulfate, and the solvent was removed under reduced pressure. The residue was subjected to purification by silica gel chromatography using, as the developer, hexane-ethyl acetate mixtures (4:1–2:1) to give 2.15 g of 4-nitrophenyl ester of 3'-(3-azidopropyloxy)-4'-methoxycinnamic acid [Compound (18)]. The obtained compound was recrystallized from ethanol to give 2.01 g of Compound (18) (yield: 87%).

$^1$HNMR spectrum (100 MHz, in $CDCl_3$) δ (ppm): 8.30 (1H, d, J=9.2 Hz), 8.17 (2H, d, J=9.2 Hz), 7.84 (1H, d, J=15.8 Hz), 7.37 (1H, d, J=9.0 Hz), 7.16 (1H, s), 6.90 (2H, d, J=9.2 Hz), 6.47 (1H, d, J=15.8 Hz), 4.15 (1H, t, J=6.2 Hz), 3.92 (3H, s), 3.57 (2H, t, J=6.5 Hz), 2.12 (2H, m)

To 12 mg (0.3 mmol) of 60% sodium hydride were added 0.6 ml of DMF, and then 1.5 ml of a solution of 60 mg (0.23 mmol) of Compound (10) in DMF, followed by stirring in an atmosphere of argon at 0° C. for 2 hours. After the resulting mixture was cooled to −20° C., 1.5 ml of a solution of 124 mg (0.31 mmol) of Compound (18) in DMF was added thereto, followed by stirring at −20 to 0° C. for 2 hours. To the resulting mixture was added 0.2 M phosphate buffer (pH 7), and then the mixture was extracted with ethyl acetate. The ethyl acetate layer was washed with a saturated aqueous solution of sodium chloride and dried over anhydrous sodium sulfate, and the solvent was removed under reduced pressure. The residue was subjected to purification using 30 ml of silica gel, and as the developer, a chloroform-methanol mixture (50:1) to give 77 mg of Compound (19) (yield: 65%).

$^1$HNMR spectrum (270 MHz, in $CDCl_3$) δ (ppm): 9.81 (1H, br), 7.68 (1H, d, J=15.5 Hz), 7.11 (1H, dd, J=8.3, 2.0 Hz), 7.01 (1H, d, J=2.0 Hz), 6.81 (1H, d, J=8.2 Hz), 6.66 (1H, d, J=15.5 Hz), 6.56 (1H, br), 4.15 (1H, d, J=11.2 Hz), 4.07 (2H, t, J=3.6 Hz), 4.06 (1H, m), 3.84 (3H, s), 3.76 (3H, s), 3.50 (2H, t, J=6.6 Hz), 3.46 (1H, m), 2.52 (3H, s), 2.31 (1H, dd, J=7.3, 3.3 Hz), 2.05 (2H, m), 1.25 (1H, dd, J=5.3, 3.4 Hz); Infrared absorption spectrum (KBr): 2098, 1697, 1622, 1608, 1516, 1392, 1263, 1217 $cm^{-1}$; Mass spectrum (SIMS): 518 (M+H)

In 1.5 ml of THF was dissolved 15 mg (0.029 mmol) of Compound (19), and 23 mg (0.088 mmol) of triphenylphosphine was added thereto, followed by stirring at room temperature for 30 minutes. To the resulting solution was added 1.5 ml of water, followed by stirring at room temperature for 24 hours. After addition of a saturated aqueous solution of sodium hydrogencarbonate, the reaction mixture was extracted with chloroform. The chloroform layer was washed with a saturated aqueous solution of sodium chloride and dried over anhydrous sodium sulfate, and the solvent was removed under reduced pressure. The residue was subjected to purification using 30 ml of silica gel, and as the developer, a chloroform-methanol-triethylamine mixture (200:10:1) to give 4 mg of Compound (20) (yield: 28%).

$^1$HNMR spectrum (270 MHz, in DMSO-$d_6$) δ (ppm): 7.75 (1H, d, J=15.2 Hz), 7.54 (1H, brs), 7.49 (1H, br, J=8.6 Hz), 7.18 (1H, d, J=8.6 Hz), 7.09 (1H, d, J=15.2 Hz), 7.03 (1H, br), 4.15 (1H, brd, J=11.2 Hz), 4.39 (1H, m), 4.27 (2H, t, J=3.6 Hz), 3.96 (3H, s), 3.87 (3H, s) 3.61 (1H, m), 3.12 (2H, t, J=7.2 Hz), 2.61 (3H, s), 2.23 (1H, m), 2.16 (2H, m), 1.46 (1H, m); Infrared absorption spectrum (KBr): 1647, 1610, 1512, 1458, 1394, 1385, 1294, 1219 $cm^{-1}$; Mass spectrum (SIMS): 492 (M+H)

REFERENCE EXAMPLE 18
Compound (X-2): BzlO-PEG-Ala-Pro-Compound (12)

In 3.5 ml of methylene chloride was dissolved 21 mg (24.5 μmol) of Compound (VIII-2) obtained in Reference Example 2, and 3.4 mg of HONSu and 6.3 mg of DCC were successively added thereto under ice cooling, followed by stirring for 2 hours. After the insoluble matter was removed by filtration, the solvent was removed from the filtrate under reduced pressure. The residue was dissolved in 3.4 ml of pyridine, followed by addition of a solution of 9.9 mg (19 μmol) of Compound (12) obtained in Reference Example 15 in 2.0 ml of pyridine under ice cooling. The resulting mixture was stirred under ice cooling for one hour and then at room temperature for 2 hours. After the solvent was removed under reduced pressure, the residue was subjected to purification using 10 ml of silica gel (Wako Gel C-200), and as the developer, 10 ml each of chloroform-methanol mixtures (100:1, 80:1, 60:1, 40:1, 20:1, 10:1, 5:1). The eluate was taken in 1.0 ml fractions. The solvent was removed from the desired fractions under reduced pressure to give 10.0 mg (7.3 μmol) of BzlO-PEG-Ala-Pro-Compound (12) (yield: 39%).

Silica gel thin layer chromatography: Kieselgel 60 (Merck & Co., Inc.); Chloroform:methanol=10:1; Rf value: 0.5; $^1$HNMR spectrum (500 MHz, in CDCl$_3$) δ (ppm): BzlO-PEG-Ala-Pro moiety 7.36 (5H, m, C$_6$H$_5$), 5.19 (2H, s, CH$_2$), 4.50 [2H, brm, CH$_2$(Pro)], 4.12 (4H, s, OCH$_2$), 3.64 (4nH, brs, OCH$_2$CH$_2$), 3.42 [2H, br, CH$_2$(Pro)], 3.23 [1H, s, CH(Ala)], 2.37 [1H, br, CH(Pro)], 2.08 [2H, brm, CH$_2$(Pro)], 1.17 [3H, d, J=2.8 Hz, CH$_3$(Ala)], Compound (12) moiety 11.58 (1H, brs, 1-NH), 9.40 (1H, brs, 1'-NH), 7.12 (1H, s, H-7), 6.95 (1H, d, J=2.3 Hz, H-3'), 6.81 (1H, s, H-4'), 4.45 (2H, m, H-5), 4.08 (3H, s, 7'-OCH$_3$), 3.92 (2H, t, J=5.2 Hz, OCH$_2$), 3.90 (3H, s, 5'-OCH$_3$), 3.82 (3H, s, 3-COOCH$_3$), 3.67 (1H, m, H-4a), 3.20 (2H, q, J=6.4 Hz, CH$_2$), 2.63 (3H, s, 2-CH$_3$), 2.38 (1H, dd, J=7.5, 3.4 Hz, H-4), 1.37 (1H, t, J=4.2 Hz, H-4); Infrared absorption spectrum (in chloroform): 3595, 3450, 3010, 2900, 1750, 1665, 1608, 1515, 1460, 1310, 1110 cm$^{-1}$

REFERENCE EXAMPLE 19
Compound (25)

Compound (25) was synthesized according to the following reaction steps.

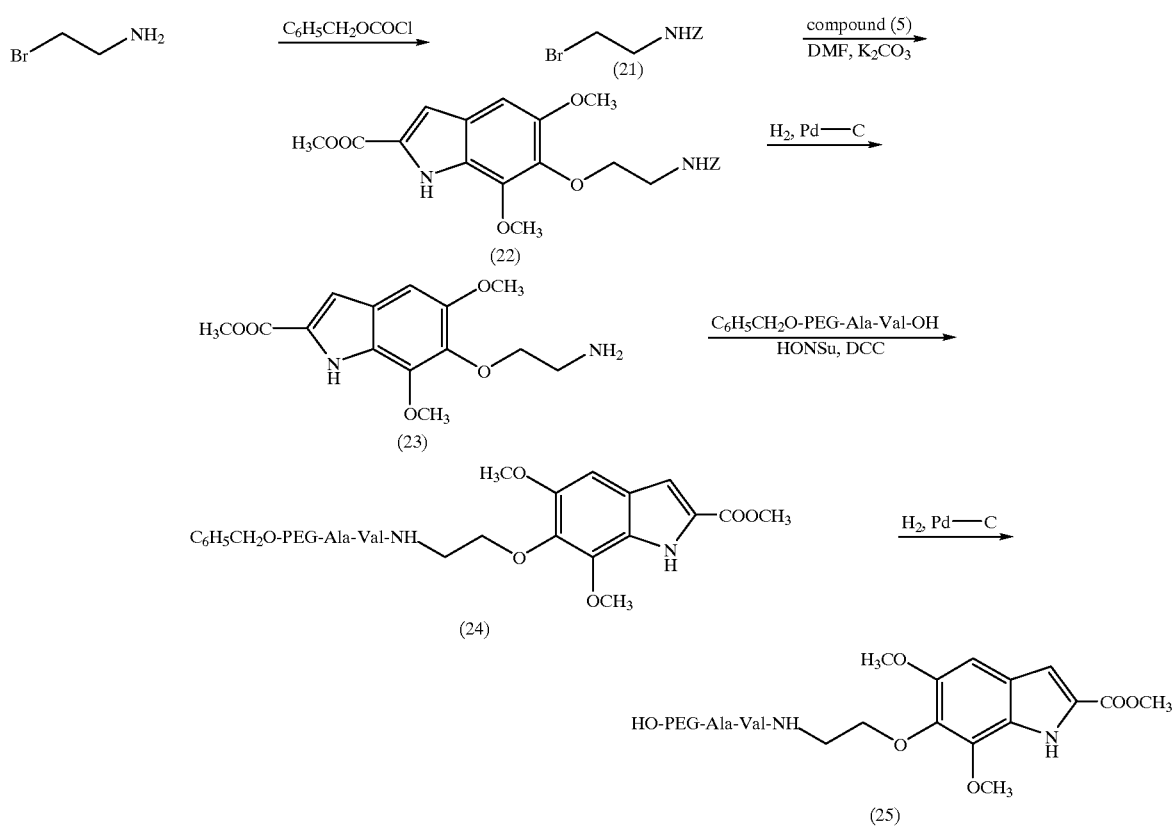

In 75 ml of methylene chloride was dissolved 3.1 g (15 mmol) of 2-bromoethylamine hydrobromide, and the solution was cooled to −40 to −50° C. After 2.6 ml (18 mmol) of benzyloxycarbonyl chloride was added dropwise thereto, the temperature of the mixture was allowed to rise to room temperature over 24 hours. Then, the solvent was removed under reduced pressure, and 50 ml of ethyl acetate and 50 ml of 1N HCl were added to the residue, followed by stirring at room temperature for 6 hours. The ethyl acetate layer was washed with 50 ml of a saturated aqueous solution of sodium chloride and dried over anhydrous sodium sulfate, and the solvent was removed under reduced pressure to give 2.0 g of Compound (21) (yield: 53%).

In 10 ml of DMF was dissolved 495 mg (2.0 mmol) of Compound (5), and 545 mg of anhydrous potassium carbonate and 1020 mg (4.0 mmol) of Compound (21) were successively added thereto, followed by stirring under ice cooling for 24 hours. To the resulting solution were successively added 100 ml of a phosphate buffer (20 mmol, pH 7.0)

and 100 ml of ethyl acetate to extract the ethyl acetate layer. The ethyl acetate layer was washed with a saturated aqueous solution of sodium chloride and dried over anhydrous sodium sulfate, and the solvent was removed under reduced pressure. The residue was subjected to purification using 100 ml of silica gel (Wako Gel C-200), and as the developer, 200 ml each of hexane-ethyl acetate mixtures (5:1, 4:1, 3:1). The eluate was taken in 10 ml fractions. The solvent was removed from the desired fractions under reduced pressure, the desired fractions being identified by silica gel thin layer chromatography [Kieselgel 60 (Merck & Co., Inc.), hexane-:ethyl acetate=2:1, Rf value: 0.2], whereby 713 mg (1.7 mmol) of Compound (22) was obtained (yield: 83%).

To 66 mg (0.15 mmol) of Compound (22) were added 1.5 ml of THF and 1.5 ml of methanol, and 6.6 mg of 10% palladium carbon catalyst was added thereto, followed by vigorous stirring in a stream of hydrogen for 18 hours. To the resulting mixture was added 6.6 mg of the catalyst, followed by further stirring for 5 hours. After the catalyst was removed by filtration, the solvent was removed from the filtrate under reduced pressure to give 36 mg (0.12 mmol) of Compound (23) (Segment B) (yield: 82%).

Silica gel thin layer chromatography: Kieselgel 60 Chloroform:methanol=5:1; Rf value: 0.3

In 1.5 ml of methylene chloride was dissolved 109 mg (0.13 mmol) of Compound (VIII-1) obtained in Reference Example 1, and 21 mg of HONSu and 38 mg of DCC were successively added thereto under ice cooling, followed by stirring under ice cooling for 3 hours. After the insoluble matter (DCU) was removed by filtration, the solvent was removed from the filtrate under reduced pressure. To the residue was added 1 ml of methylene chloride, and 1 ml of a solution of 34 mg (0.12 mmol) of Compound (23) in methylene chloride was added thereto under ice cooling. The temperature of the mixture was allowed to rise to room temperature with stirring for 24 hours. After the insoluble matter (DCU) was removed by filtration, the solvent was removed from the filtrate under reduced pressure to obtain 192 mg of a residue. The residue was subjected to purification using 20 ml of silica gel (Wako Gel C-200), and as the developer, 20 ml each of chloroform-methanol mixtures (100:0, 100:1, 50:1, 30:1, 20:1). The eluate was taken in 5 ml fractions. The solvent was removed from the desired fractions under reduced pressure, the desired fractions being identified by silica gel thin layer chromatography [Kieselgel 60 (Merck & Co., Inc.), chloroform:methanol=10:1, Rf value: 0.4], whereby 89 mg (0.08 mmol) of Compound (24) was obtained (yield: 68%). The structures of Compounds (21) to (23) were confirmed by $^1$HNMR and mass spectrometric analysis, and the structure of Compound (24) was confirmed by $^1$HNMR.

In a mixture of 2 ml of THF and 2 ml of methanol was dissolved 89 mg (79 μmol) of Compound (24), and 18 mg of 10% palladium carbon catalyst was added thereto, followed by vigorous stirring in a stream of hydrogen for 15 hours. After addition of 9 mg of the catalyst, the mixture was stirred in a stream of hydrogen for 9 hours. Then, 9 mg of the catalyst was added again, followed by stirring in a stream of hydrogen for 15 hours. After the catalyst was removed by filtration, the solvent was removed from the filtrate under reduced pressure. The residue was subjected to purification using 10 ml of silica gel (Wako Gel C-200), and as the developer, chloroform-methanol mixtures (100:0, 50:1, 30:1). The eluate was taken in 5 ml fractions. The solvent was removed from the desired fractions under reduced pressure, the desired fractions being identified silica gel thin layer chromatography, whereby 52 mg of Compound (25) was obtained (yield: 63%).

Silica gel thin layer chromatography: Kieselgel 60 (Merck & Co., Inc.); Chloroform:methanol=5:1; Rf value: 0.4; $^1$HNMR spectrum (500 MHz, in CDCl$_3$) δ (ppm): PEG-Ala-Val moiety 4.13 (4H, s, OCH$_2$), 3.64 (4nH, brs, OCH$_2$CH$_2$), 3.23 [1H, s, CH(Ala)], 2.22 [1H, brq, J=6.0 Hz, CH(Val)], 1.26 [1H, s, CH(Val)], 1.17 [3H, d, J=2.8 Hz, CH$_3$(Ala)], 0.89 [6H, q, J=2.5 Hz, CH$_3$(Val)], Segment B moiety 9.40 (1H, brs, 1-NH), 6.95 (1H, d, J=2.2 Hz, H-3), 6.82 (1H, s, H-4), 4.08 (3H, s, 7-OCH$_3$), 3.92 (2H, d, J=5.2 Hz, OCH$_2$), 3.90 (3H, s, 5-OCH$_3$), 3.85 (3H, s, 2-COOCH$_3$), 3.20 (2H, q, J=6.4 Hz, CH$_2$)

REFERENCE EXAMPLE 20

KM-641-(PEG-Ala-Val-Segment B)$_m$

In 0.8 ml of methylene chloride was dissolved 7.8 mg (7.5 μmol) of Compound (25) obtained in Reference Example 19, and 1.0 ml of a solution of HONSu in methylene chloride (1 mg/ml) and 0.9 ml of a solution of DCC in methylene chloride (2 mg/ml) were successively added thereto under ice cooling, followed by stirring at room temperature for 3 hours. After the solvent was removed under reduced pressure, 1 ml of DMSO was added to the residue. The resulting mixture was added under ice cooling to a solution prepared by adding 11.5 ml of a phosphate buffer to 8 ml of an aqueous solution of KM-641 antibody (1.47 mg/ml), followed by gentle stirring at 4° C. for 24 hours. After the insoluble matter was removed with a filter (0.22 μm), the antibody fraction was purified by gel filtration chromatography [column: 200 ml of Sephacryl S 200 (Pharmacia Co., Ltd.), developer: a phosphate buffer, flow rate: 0.5 ml/minute, 11.5 ml fractions]. The 8th and 9th fractions were collected to obtain a solution containing 0.34 mg/ml KM-641-(PEG-Ala-Val-Segment B)$_m$.

The number of molecules of Segment B bound per antibody molecule was calculated by subjecting the conjugate to enzyme treatment (thermolysin) and quantitatively determining released H-Val-Segment B by HPLC according to the method described in Reference Example 22. It was found that in the obtained conjugate, the number of molecules of Segment B was 1.9 per antibody molecule.

It was confirmed that the affinity of the conjugate was approximately equal to that of an unbound antibody according to the following enzyme-linked immunosorbent assay.

<Measurement of an affinity of an antibody by ELISA (Enzyme-linked Immunosorbent Assay)>

Ganglioside GD$_3$ (2 nmol) was dissolved in 2 ml of ethanol containing 5 ng of phosphatidyl choline (Sigma Chemical Co.) and 2.5 ng of cholesterol, and the solution was put into wells of a 96-well plate for ELISA (Linbro Co., Ltd.) in an amount of 20 μl/well. After drying the wells, a phosphate buffer containing 1% bovine serum albumin was added to the wells for blocking. The above-described conjugate (10 μg/ml, 50 μl) was added to each well, and the plate was allowed to stand at room temperature for 2 hours (or at 4° C. for 24 hours). Then peroxidase-labelled rabbit anti-mouse Ig antibody (Dako) was added to the wells as the second antibody, and the plate was allowed to stand at room temperature for 1 to 2 hours, followed by washing. ABTS (Sigma Chemical Co.) solution was added, and after the color developed, spectrophotometry was carried out on the absorbance at 414 nm using NJ-2001 (Japan Intermed Co., Ltd.).

REFERENCE EXAMPLE 21

Enzyme-specific Cleavage of a Spacer Experiment using a spacer bound to Segment B (side chain model)

This Reference Example demonstrates that the peptide bond of a spacer bound to an antitumor agent is cleaved in a cell by a specific enzyme and that the cleavage of the spacer does not occur in a serum, using Compound (25) obtained in Reference Example 19. The release of Segment B by the use of thermolysin as the cleavage enzyme was confirmed in the following manner.

To 0.1 ml of a solution of Compound (25) in a phosphate buffer (0.2 mg/ml) was added 0.1 ml of an enzyme solution (0.1 mg/ml) (amount of enzyme: 94 pU), and the mixture was allowed to stand at 37° C. for 24 hours. The amount of H-Val-Segment B released from Compound (25) was checked by analyzing the supernatant by reversed-phase HPLC (cleavage efficiency: 100%).

Reversed-phase HPLC conditions;

Apparatus: UVIDEC-100IV Spectrophotometric detector, TRIROTAR SR (Japan Spectroscopic Co., Ltd.); Column: UNISIL PACK 5C18-150A (GL Sciences); Eluent: 50 mM acetate buffer (pH 4.5) [10–70% acetonitrile gradient (35 minutes)]; Flow rate: 0.7 ml/minute; Detection wavelength: 300 nm; Elution time: 39.0 minutes; Mass spectrum (SIMS): 393.2 (M+H); Amino acid analysis: Val 1.0 (1.0)

It was confirmed as follows that the spacer was not cleaved in a serum.

To 0.1 ml of a solution of Compound (25) in a phosphate buffer (0.2 mg/ml) was added 0.1 ml of a human serum, and the mixture was allowed to stand at 37° C. for 2 days. The resulting supernatant was analyzed by reversed-phase HPLC under the same conditions as in the above experiment, except that 50 mM phosphate buffer (pH 5.9) was used as the eluent. As a result, the peak derived from Segment B was not confirmed.

REFERENCE EXAMPLE 22

Enzyme-specific Cleavage of a Spacer Experiment using a conjugate of an antibody and Segment B through a spacer (side chain model)

This Reference Example demonstrates that the peptide bond of a conjugate of an antibody and an antitumor agent through a spacer is cleaved in a cell by a specific enzyme, but is stable in a serum, using the conjugate of an antibody and Segment B through a spacer obtained in Reference Example 20. The specific cleavage of the spacer was confirmed as follows using thermolysin as the intracellular cleavage enzyme and plasmin as the main proteolytic enzyme in blood.

To 250 μl of KM-641-(PEG-Ala-Val-Segment B)$_m$ (0.33 mg/ml) were added 2.5 μl of thermolysin (0.1 mg/ml) (amount of enzyme: 2.4 pU) [or 2.5 μl of a 1:200 dilution of plasmin (amount of enzyme: 250 μU)] and 5.7 μl of a phosphate buffer, and the mixture was allowed to stand at 37° C. for 24 hours. The resulting supernatant was analyzed by reversed-phase HPLC under the same conditions as in Reference Example 21.

The peak of H-Val-Segment B similar to that in Reference Example 21 was confirmed 42.0 minutes after the elution started for the conjugate treated with thermolysin, but the peak was not confirmed for the conjugate treated with plasmin. Plasmin being one of the main proteolytic enzymes in blood, these results show that the conjugate is stable in blood, but when it is incorporated into a cell, its antitumor agent moiety is specifically cleaved by a specific enzyme to express an antitumor activity.

REFERENCE EXAMPLE 23

Enzyme-specific Cleavage of a Spacer Experiment using a spacer bound to Compound (12)

(1) Cleavage of Compound (X-1) [BzlO-PEG-Ala-Val-Compound (12)] with thermolysin In 10 μl of DMSO was dissolved 20 μg (15 nmol) of Compound (X-1) obtained in Reference Example 16, and 90 μl of a phosphate buffer was added thereto. To the resulting mixture was added 100 μl of a thermolysin solution (2 mg/ml) (amount of enzyme: 1.9 μU), and the mixture was allowed to stand at 37° C. for 5 hours. The resulting supernatant was analyzed by reversed-phase HPLC, whereby the release of H-Val-Compound (12) from Compound (X-1) (elution time: 35.1 minutes) was confirmed (cleavage efficiency: 78%).

Reversed-phase HPLC conditions; Apparatus: The same as in Reference Example 21; Eluent: A solution containing 25% buffer (pH 4.8) prepared from a 0.2 M aqueous solution of disodium hydrogenphosphate and a 0.1 M aqueous solution of citric acid [10–70%. acetonitrile gradient (35 minutes)]; Flow rate: 0.7 ml/minute; Detection wavelength: 330 nm; Elution time: 31.6 minutes; Mass spectrum (SIMS): 620 (M+H); Amino acid analysis: Val 1.0 (1.0)

(2) Cleavage of Compound (X-2) [BzlO-PEG-Ala-Pro-Compound (12)] with proline endopeptidase To 54 μg (40 nmol) of Compound (X-2) obtained in Reference Example 18 were added 20 μl of DMSO and 370 μl of a phosphate buffer. After 10 μl of a proline endopeptidase solution (0.1 mg/ml) was added, the mixture was allowed to stand at 37° C. for 2.5 hours. The resulting supernatant was analyzed by reversed-phase HPLC, whereby the release of Compound (12) from Compound (X-2) was confirmed (cleavage efficiency: 100%).

Reversed-phase HPLC conditions;

Apparatus: The same as in Reference Example 21; Eluent: 50 mM phosphate buffer (pH 5.9) (10–70% acetonitrile gradient); Flow rate: 0.7 ml/minute; Detection wavelength: 330 nm; Elution time: 30.6 minutes [agreed with that for Compound (12)]; Mass spectrum (SIMS): 521 (M+H)

REFERENCE EXAMPLE 24

Enzyme-specific Cleavage of a Spacer Experiment using a conjugate of an antibody and Compound (12) through a spacer To 740 μl of Compound (Ia-11) {KM-641-[PEG-Ala-Val-Compound (12)]$_m$} obtained in Example 11 (0.07 mg/ml) was added 5.1 μl of a thermolysin solution (0.1 mg/ml) (amount of enzyme: 26 μU), and the mixture was allowed to stand at 37° C. for 8 hours. The resulting supernatant was analyzed by reversed-phase HPLC under the same conditions as in Reference Example 23 (1), whereby the release of H-Val-Compound (12) from Compound (Ia-11) was confirmed.

Elution time: 31.6 minutes; Mass spectrum (SIMS): 620 (M+H)

REFERENCE EXAMPLE 25

Enzyme-specific Cleavage of a Spacer Experiment using a spacer bound to adriamycin (1) Cleavage of Compound (XI-3) (HO-PEG-Gly-Pro-ADM) with proline endopeptidase In 20 μl of DMSO was dissolved 14.3 μg (11 nmol) of Compound (XI-3) obtained in Reference Example 8, and 210 μl of a phosphate buffer was added thereto. To the resulting mixture was added 80 μl of proline endopeptidase (1.0 mg/ml) (amount of enzyme: 2.8 U), and the mixture was allowed to stand at 37° C. for 24 hours. The resulting supernatant was analyzed by reversed-phase HPLC, whereby the release of ADM from Compound (XI-3) (elution time: 23.3 minutes) was confirmed (cleavage efficiency: 50%).

Reversed-phase HPLC conditions; Eluent: 50 mM phosphate buffer (pH 5.9) [10–70% acetonitrile gradient (35 minutes)]; Flow rate: 0.7 ml/minute; Detection wavelength: 233 nm; Elution time: 24.0 minutes (agreed with that for ADM); Mass spectrum (SIMS): 544.2 (M+H) (agreed with that for ADM)

(2) Cleavage of Compound (XI-1) (HO-PEG-Ala-Val-ADM) with thermolysin

In 10 μl of DMSO was dissolved 0.09 mg (10.2 nmol) of Compound (XI-1) obtained in Example 6, and 210 μl of a phosphate buffer was added thereto. To the resulting mixture was added 80 μl of thermolysin (1.0 mg/ml) (amount of enzyme: 750 pU), and the mixture was allowed to stand at 37° C. for 24 hours. The resulting supernatant was analyzed by reversed-phase HPLC under the same conditions as in (1), whereby the release of H-Val-ADM from Compound (XI-1) (elution time: 23.8 minutes) was confirmed (cleavage efficiency: 100%).

Elution time: 25.2 minutes; Mass spectrum (SIMS): 643 (M+H)

REFERENCE EXAMPLE 26

Enzyme-specific Cleavage of a Spacer Experiment using a conjugate of an antibody and adriamycin through a spacer (1) Cleavage of Compound (Ia-3) [NL-1-(PEG-Gly-Pro-ADM)$_m$] with proline endopeptidase To 35 μl of Compound (Ia-3) obtained in Example 3 (0.19 mg/ml) were added 70 μl of proline endopeptidase (1.0 mg/ml) (amount of enzyme: 2.4 U) and 95 μl of a phosphate buffer, and the mixture was allowed to stand at 37° C. for 24 hours. The resulting supernatant was analyzed by reversed-phase HPLC under the same conditions as in Reference Example 25, whereby the release of ADM from Compound (Ia-3) was confirmed (cleavage efficiency: 10%).

Elution time: 23.7 minutes (agreed with that for ADM)

(2) Cleavage of Compound (Ia-1) [NL-1-(PEG-Ala-Val-ADM)$_m$] with thermolysin

To 50 μl of Compound (Ia-1) obtained in Example 1 (0.42 mg/ml) were added 50 μl of thermolysin (2.0 mg/ml) (amount of enzyme: 0.9 μU) and 100 μl of a phosphate buffer, and the mixture was allowed to stand at 37° C. for 24 hours. The resulting supernatant was analyzed by reversed-phase HPLC under the same conditions as in Reference Example 25, whereby the release of H-Val-ADM from Compound (Ia-1) was confirmed (cleavage efficiency: 100%).

Elution time: 28.1 minutes (3) Cleavage of Compound (Ia-2) [NL-1-(PEG-Ala-Pro-ADN)$_m$] with proline endopeptidase To 40 μl of Compound (Ia-2) obtained in Example 2 (0.27 mg/ml) were added 110 μl of proline endopeptidase (1.0 mg/ml) (amount of enzyme: 3.9 U) and 50 μl of a phosphate buffer, and the mixture was allowed to stand at 37° C. for 24 hours. The resulting supernatant was analyzed by reversed-phase HPLC under the same conditions as in Reference Example 25, whereby the release of ADM from Compound (Ia-2) was confirmed (cleavage efficiency: 10%).

Elution time: 23.9 minutes (agreed with that for ADM)

REFERENCE EXAMPLE 27

Enzyme-specific Cleavage of a Spacer Experiment using a conjugate of an antibody and Compound (20) through a spacer (1) Cleavage of Compound (Ia-9) {NL-1-[PEG-Gly-Pro-Compound (20)]$_m$} with proline endopeptidase To 17 μl of Compound (Ia-9) obtained in Example 9 (1.2 mg/ml) were added 80 μl of proline endopeptidase (1.0 mg/ml) (amount of enzyme: 2.8 U) and 53 μl of a phosphate buffer, and the mixture was allowed to stand at 37° C. for 24 hours. The resulting supernatant was analyzed by reversed-phase HPLC, whereby the release of Compound (20) from Compound (Ia-9) was confirmed.

Reversed-phase HPLC conditions; The same apparatus and column as in Reference Example 21 were used. Eluent: 50 mM phosphate buffer (pH 7.0) [10–70% acetonitrile gradient (35 minutes)]; Flow rate: 0.7 ml/minute; Detection wavelength: 330 nm; Elution time: 26.0 minutes [agreed with that for Compound (20)]

(2) Cleavage of Compound (Ia-7) {NL-1-[PEG-Ala-Val-Compound (20)]$_m$} with thermolysin To 18 μl of Compound (Ia-7) obtained in Example 7 (1.1 mg/ml) were added 60 μl of thermolysin (3.0 mg/ml) (amount of enzyme: 1.7 μU) and 72 μl of a phosphate buffer, and the mixture was allowed to stand at 37° C. for 24 hours. The resulting supernatant was analyzed by reversed-phase HPLC under the same conditions as in (1), whereby the release of H-Val-Compound (20) from Compound (Ia-7) was confirmed.

Elution time: 17.7 minutes (3) Cleavage of Compound (Ia-8) {NL-1-[PEG-Ala-Pro-Compound (20)]$_m$} with proline endopeptidase To 11 μl of Compound (Ia-B) obtained in Example 8 (1.8 mg/ml) were added 80 μl of proline endopeptidase (1.0 mg/ml) (amount of enzyme: 2.8 U) and 59 μl of a phosphate buffer, and the mixture was allowed to stand at 37° C. for 24 hours. The resulting supernatant was analyzed by reversed-phase HPLC under the same conditions as in (1), whereby the release of Compound (20) from Compound (Ia-8) was confirmed.

Elution time: 25.9 minutes [agreed with that for Compound (20)]

REFERENCE EXAMPLE 28

Compound (IIa-1): HO-PEG-Ala-Val-OH

In 5.0 ml of methanol was dissolved 100 mg (117 μmol) of Compound (VIII-1) obtained in Reference Example 1 in a stream of nitrogen, and 20 mg of 10% palladium carbon catalyst was added thereto, followed by vigorous stirring in a stream of hydrogen at room temperature for 2 hours. After the catalyst was removed by filtration, the solvent was removed from the filtrate under reduced pressure to give 76 mg (99 μmol) of HO-PEG-Ala-Val-OH (yield: 85%).

$^1$HNMR spectrum (100 MHz, in CDCl$_3$) δ (ppm): 4.12 (4H, s, OCH$_2$), 3.64 (4nH, brs, OCH$_2$CH$_2$), 3.23 [1H, s, CH(Ala)], 2.23 [1H, brq, J=6.0 Hz, CH(Val)], 1.26 [1H, s, CH(Val)], 1.17 [3H, d, J=2.8 Hz, CH$_3$(Ala)], 0.89 (6H, brd, J=2.5 Hz, CH$_3$(Val)]

REFERENCE EXAMPLE 29

Compound (IIa-2): HO-PEG-Ala-Pro-OH

In 5.0 ml of methanol was dissolved 100 mg (117 μmol) of Compound (VIII-2) obtained in Reference Example 2 in a stream of nitrogen, and 20 mg of 10% palladium carbon catalyst was added thereto, followed by vigorous stirring in a stream of hydrogen at room temperature for 3 hours. After the catalyst was removed by filtration, the solvent was removed from the filtrate under reduced pressure to give 70 mg (91 μmol) of HO-PEG-Ala-Pro-OH (yield: 78%).

$^1$HNMR spectrum (100 MHz, in CDCl$_3$) δ (ppm): 4.40 [2H, br, CH$_2$(Pro)], 4.12 (4H, s, OCH$_2$), 3.80 [1H, q, J=6.0 Hz, CH(Ala)], 3.64 (4nH, brs, OCH$_2$CH$_2$), 3.59 [2H, br, CH$_2$(Pro)], 2.36 [1H, br, CH(Pro)], 2.02 [2H, br, CH$_2$(Pro)], 1.29 [3H, brd, J=3.5 Hz, CH$_3$(Ala)]

REFERENCE EXAMPLE 30

Compound (IIa-3): HO-PEG-Gly-Pro-OH

In 5.0 ml of methanol was dissolved 100 mg (116 μmol) of Compound (VIII-3) obtained in Reference Example 3 in a stream of nitrogen, and 20 mg of 10% palladium carbon catalyst was added thereto, followed by vigorous stirring in a stream of hydrogen at room temperature for 2 hours. After the catalyst was removed by filtration, the solvent was removed from the filtrate under reduced pressure to give 76 mg (98 μmol) of HO-PEG-Gly-Pro-OH (yield: 85%).

$^1$HNMR spectrum (100 MHz, in CDCl$_3$) δ (ppm): 4.40 [2H, br, CH$_2$(Pro)], 4.12 (4H, s, OCH$_2$), 3.82 [2H, s, CH$_2$(Gly)], 3.64 (4nH, brs, OCH$_2$CH$_2$), 3.59 [2H, br, CH$_2$(Pro)], 2.21 [1H, s, CH(Pro)], 2.02 [2H, br, CH$_2$(Pro)]

INDUSTRIAL APPLICABILITY

The present invention provides a toxin conjugate which is useful as an active ingredient of an antitumor agent and an in vitro diagnosis technique using the conjugate. The conjugate comprises a toxin and a compound having an affinity for a target cell, for example, an antibody or antibody fragment which is specific to a cancer, said toxin and compound being bound through a spacer.

What is claimed is:

1. A toxin conjugate in which a compound having an affinity for a target cell is bound to a toxin through a spacer consisting essentially of polyalkylene glycol and a dipeptide.

2. A toxin conjugate represented by formula (I)

wherein Z represents a compound having an affinity for a target cell and having a group capable of binding to $X^1$; $X^1$ represents CO, S or

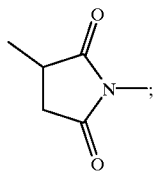

W represents a single bond or

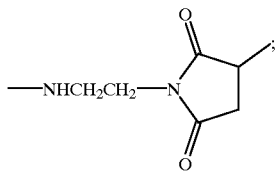

$Y^1$ represents a toxin; $R^1$ and $R^2$, which may be the same or different, each represents an amino acid residue; n represents an integer of 1–1000; and m represents an integer of 1–100.

3. The toxin conjugate according to claim 2, wherein the group capable of binding to $X^1$ is CO, N, S or O, and $Y^1$ has a group selected from N, S or O, provided that when $X^1$ is S, Z is bound to $X^1$ via CO of Z, and when $X^1$ is a group other than S, Z is bound to $X^1$ via N, S or O of Z, and $Y^1$ is bound to W or $R^2$ through N, S or O of $Y^1$.

4. The toxin conjugate according to claim 2 or 3, wherein Z is a protein or a peptide.

5. The toxin conjugate according to claim 4, wherein the protein is an antibody or an antibody fragment.

6. The toxin conjugate according to claim 2 wherein $R^1$ represents an alanine residue, a leucine residue, or a glycine residue; and $R^2$ represents a proline residue, a valine residue, or a leucine residue.

7. The toxin conjugate according to claim 2 wherein $Y^1$ is adriamycin, daunorubicin, a duocarmycin derivative, mitomycin A, mitomycin C, ricin A, diphtheria toxin, or Pseudomonas exotoxin.

8. A toxin conjugate according to claim 2, wherein said compound having an affinity for a target cell has a group capable of binding to $X^1$ selected from the group consisting of COOH, NH, SH and OH.

9. A toxin conjugate according to claim 1, wherein said toxin conjugate has a structure selected from the group consisting of NL-1-(PEG-Ala-Val-ADM)m
NL-1-(PEG-Ala-Pro-ADM)m
NL-1-(PEG-Gly-Pro-ADM)m
KM-231-(PEG-Ala-Val-DNR)m
KM-231-(PEG-Ala-Pro-DNR)m
KM-231-(PEG-Gly-Pro-DNR)m
NL-1-(PEG-Ala-Val-Compound (20))m
NL-1-(PEG-Ala-Pro-Compound (20))m
NL-1-(PEG-Gly-Pro-Compound (20))m
KM-231-(PEG-Ala-Val-Compound 12)m
KM-631-(PEG-Ala-Val-Compound 12)m,
wherein NL-1, MK-231 and KM-631 are monoclonal antibodies, and ADM is adriamycin and DNR is daunorubicin.

10. A toxin conjugate according to claim 3, wherein said $Y^1$ is bound to $R^2$ through N, S or O, when W represents a single bond.

11. A toxin conjugate in which a compound having an affinity for a target cell is bound to a toxin through a spacer consisting of a polyalkylene glycol and a dipeptide.

* * * * *